United States Patent
Backhed et al.

(10) Patent No.: US 9,881,135 B2
(45) Date of Patent: Jan. 30, 2018

(54) IDENTIFICATION OF A PERSON HAVING RISK FOR DEVELOPING TYPE 2 DIABETES

(71) Applicant: Metabogen AB, Gothenburg (SE)

(72) Inventors: Fredrik Backhed, Kullavik (SE); Fredrik H. Karlsson, Gothenburg (SE); Jens Nielson, Gothenburg (SE); Bjorn Fagerberg, Molnlycke (SE); Valentina Tremaroli, Gothenburg (SE)

(73) Assignee: METABOGEN AB, Gothenburg (SE)

( * ) Notice: Subject to any disclaimer, the term of this patent is extended or adjusted under 35 U.S.C. 154(b) by 413 days.

(21) Appl. No.: 14/651,550

(22) PCT Filed: Dec. 13, 2013

(86) PCT No.: PCT/EP2013/076611
§ 371 (c)(1),
(2) Date: Jun. 11, 2015

(87) PCT Pub. No.: WO2014/091017
PCT Pub. Date: Jun. 19, 2014

(65) Prior Publication Data
US 2015/0317444 A1 Nov. 5, 2015

Related U.S. Application Data

(60) Provisional application No. 61/797,701, filed on Dec. 13, 2012.

(51) Int. Cl.
*G06F 15/18* (2006.01)
*G06F 19/00* (2011.01)
(Continued)

(52) U.S. Cl.
CPC ............ *G06F 19/345* (2013.01); *G06F 19/18* (2013.01); *G06F 19/3443* (2013.01); *G06F 19/22* (2013.01); *G06F 19/24* (2013.01)

(58) Field of Classification Search
CPC combination set(s) only.
See application file for complete search history.

(56) References Cited

U.S. PATENT DOCUMENTS 9,040,101 B2 * 5/2015 Heiman ............... A61K 31/733
424/725
9,173,910 B2 * 11/2015 Kaplan ................ A61K 35/741
(Continued)

OTHER PUBLICATIONS

Shared genetic architecture in autoimmune disease—preliminary analysis Leqi Liu; Jia Tao; Ziyan Yang; Fadi Towfic 2015 IEEE International Conference on Bioinformatics and Biomedicine (BIBM) Year: 2015 pp. 800-806 IEEE Conference Publications.*
(Continued)

*Primary Examiner* — Michael B Holmes
(74) *Attorney, Agent, or Firm* — Myers Bigel, P.A.

(57) ABSTRACT

The present invention relates to the identification of a person having risk for developing type 2 diabetes (T2D) by determining the presence or absence of specific genes, gene clusters, genera or species of bacteria in the person's gastrointestinal microbiota. More specifically the invention relates to a model to identify an individual having or at risk of developing type 2 diabetes (T2D) using metagenomic clusters (MGCs), wherein said model is characterized by using different metagenomic clusters for different population groups. Also provided is the use of such a model in the identification of a person having risk for developing type 2 diabetes (T2D).

20 Claims, 20 Drawing Sheets

(51) Int. Cl.
*G06F 19/18* (2011.01)
*G06F 19/22* (2011.01)
*G06F 19/24* (2011.01)

(56) References Cited

U.S. PATENT DOCUMENTS

| | | | | |
|---|---|---|---|---|
| 9,386,793 | B2* | 7/2016 | Blaser | A61K 35/741 |
| 9,463,169 | B2* | 10/2016 | Heiman | A61K 31/733 |
| 9,757,346 | B2* | 9/2017 | Fayad | A61K 31/195 |
| 2002/0077372 | A1* | 6/2002 | Gers-Barlag | A61K 8/066 |
| | | | | 516/98 |
| 2005/0239706 | A1* | 10/2005 | Backhed | A61K 35/741 |
| | | | | 514/4.8 |
| 2015/0299776 | A1* | 10/2015 | Backhed | A61K 31/00 |
| | | | | 424/184.1 |
| 2015/0317444 | A1* | 11/2015 | Backhed | G06F 19/18 |
| | | | | 706/12 |
| 2016/0113972 | A1* | 4/2016 | Bjorck | A21D 13/02 |
| | | | | 424/400 |

OTHER PUBLICATIONS

A research of data stratification algorithm based on semi-supervised clustering Shaobo Yang; Jianmin Yu; Yi Liu 2015 IEEE International Conference on Progress in Informatics and Computing (PIC) Year: 2015 pp. 196-200 IEEE Conference Publications.*
A Novel Model for Metabolic Syndrome Risk Quantification Based on Areal Similarity Degree Sangjin Jeong; Yu Mi Jo; Sang-Oh Shim; Yeon-Jung Choi; Chan-Hyun Youn IEEE Transactions on Biomedical Engineering Year: 2014, vol. 61, Issue: 3 pp. 665-679 IEEE Journals & Magazines.*
Semi-Supervised Clustering Models for Clinical Risk Assessment Yongyang Huo; Francisco Azuaje; Paul McCullagh; Roy Harper Sixth IEEE Symposium on BioInformatics and BioEngineering (BIBE'06) Year: 2006 pp. 243-250 IEEE Conference Publications.*
International Search Report Corresponding to International Application No. PCT/EP2013/076611; dated Jul. 2, 2014.
Junjie Qin et al: "A metagenome-wide association study of gut microbiota in type 2 diabetes", *Nature,* vol. 490, No. 7418, Sep. 26, 2012, pp. 55-60.
Junjie Qin et al: "A human gut microbial gene catalogue established by metagenomic sequencing", *Nature,* vol. 464, No. 7285, Mar. 4, 2010, pp. 59-65.
Ayme Spor et al: "Unraveling the effects of the environment and host genotype on the gut microbiome", *Nature Reviews Microbiology,* vol. 9, No. 4, Apr. 1, 2011, pp. 279-290.
Fredrik H. Karlsson et al: "Gut metagenome in European women with normal, impaired and diabetic glucose control", *Nature,* vol. 498, No. 7452, May 29, 2013, pp. 99-103.

* cited by examiner

IDENTIFICATION OF A PERSON HAVING RISK FOR DEVELOPING TYPE 2 DIABETES

STATEMENT OF PRIORITY

This application is a 35 U.S.C. § 371 national phase application of International Application Serial No. PCT/EP2013/076611, filed Dec. 13, 2013, which claims the benefit of U.S. Provisional Patent Application No. 61/797,701; filed Dec. 13, 2012, the entire contents of which are incorporated by reference herein.

FIELD OF THE INVENTION

The present invention relates generally to medicine. More specifically the invention relates to the identification of a person having or having risk for developing type 2 diabetes (T2D) by determining the presence or absence of specific genes, gene clusters, genera or species of microorganisms in the person's gastrointestinal microbiota. In particular, the present invention relates to a model to identify an individual having or at risk for developing type 2 diabetes (T2D) using metagenomic clusters (MGCs), wherein said model is characterised by using different metagenomic clusters for different population groups.

BACKGROUND OF THE INVENTION

Within the body of a healthy adult, microbial cells are estimated to outnumber human cells by a factor of ten to one. These communities, however, remain largely unstudied, leaving almost entirely unknown their influence upon human development, physiology, immunity, nutrition and health.

Traditional microbiology has focused on the study of individual species as isolated units. However many, if not most, have never been successfully isolated as viable specimens for analysis, presumably because their growth is dependent upon a specific microenvironment that has not been, or cannot be, reproduced experimentally. Among those species that have been isolated, analyses of genetic makeup, gene expression patterns, and metabolic physiologies have rarely extended to inter-species interactions or microbe-host interactions. Advances in DNA sequencing technologies have created a new field of research, called metagenomics, allowing comprehensive examination of microbial communities, even those comprised of uncultivable organisms. Instead of examining the genome of an individual bacterial strain that has been grown in a laboratory, the metagenomic approach allows analysis of genetic material derived from complete microbial communities harvested from natural environments. For example, the gut microbiota complements our own genome with metabolic functions that affects human metabolism and may thus play an important role in health and disease.

Type 2 diabetes (T2D) is a metabolic disorder characterized by hyperglycemia and defects in insulin secretion and action. T2D is on the rise worldwide and an estimated 350 million people will be affected by 2030. This chronic disease is associated with multiple metabolic and cardiovascular comorbidities, and increased mortality from cardiovascular complications. Equally alarming is the fact that about half of all patients with T2D are newly detected, and many of them have cardiovascular complications at the time of diagnosis. Long before diabetes develops, impaired glucose tolerance (IGT) and other metabolic defects may appear. Since pharmacological and lifestyle interventions can reduce or postpone diabetes, especially in subjects with IGT, early detection of individuals at risk of T2D, for example individuals with IGT, is important for prevention of T2D and for reducing the costs of medical care.

T2D is a result of complex gene-environment interactions, and several risk factors have been identified, including age, family history, diet, sedentary lifestyle, and obesity. Statistical models that combine known risk factors for T2D can reasonably identify IGT and T2D individuals. However, these studies also indicate that genetic markers contribute little to the models, while socio-demographic and environmental factors have greater influence so there is a need for more accurate tools for prediction of future T2D risk.

DEFINITIONS

All terms used in the present specification are intended to have the meaning usually given to them in the art. For the sake of clarity, some terms are also defined below.

The term "bacterial group" shall be construed as meaning a group of bacteria belonging to the same genus, family, order, class, or phylum of bacteria. A bacterial group thus includes at least one bacterial species; often several different bacterial species.

Throughout the text, the term "Type 2 diabetes" (T2D) is used to refer to a metabolic disorder characterized by hyperglycemia, insulin resistance and relative impairment in insulin secretion.

The term "IGT" refers to persons with impaired glucose tolerance.

The term "NGT" refers to persons with normal glucose tolerance.

The term "metagenomics" refers to the application of modern genomics techniques to the study of communities of microbial organisms directly in their natural environments, bypassing the need for isolation and lab cultivation of individual species.

The term "MGC"/"MGCs" refers to metagenomic clusters. These are sets of highly correlated genes, (e.g. with a Pearson rho value of >0.85). MGCs are clusters of genes contained in the metagenomic DNA which co-occur in a number of individuals in a population (for example in at least 2, 5, 10, or 20 individuals) with high correlation and thus provide an indication of (or information regarding) the content of the metagenome in that population. Preferably the co-occurrence is determined statistically by analysing the gene abundance in each individual of a population and, when genes are present in a number of individuals (for example in at least 2, 5, 10 or 20 individuals) then the correlation coefficient between all possible pairs of gene abundance vectors across subjects is calculated (with the assumption that genes from the same genome should have a similar abundance in one subject), after which sets of genes with high correlation amongst them/between them (e.g. with a Pearson rho value of >0.85) are clustered in a set to form a MGC.

The clustering is done in a single stage (one stage). Clustering was done by calculating the correlation distance (1—correlation coefficient) and clustering with the Markov cluster algorithm implemented in the MCL software (Dongen, Graph Clustering by Flow Simulation, PhD thesis, Univ. Utrecht, 2000). Cluster abundance was calculated by summing the relative abundance of all genes in a cluster.

Thus MGCs can be determined by analysing the co-occurrence of genes present in a sufficient number of individuals, for example at least 2, 5, 10 or 20 individuals, to obtain a suitably high correlation value (e.g. a Pearson rho value >0.85), wherein said correlation value is obtained by calculating the correlation coefficient across subjects and then clustering sets of genes with high correlation between them/among them to provide MGCs.

Importantly, the MGCs are identified/determined from all the metagenomic sequence data from a population group as defined herein (i.e. from all the metagenomic genes of a particular population group). They are not identified/determined based on differential abundance of genes between T2D patients and normal/healthy/control individuals. Thus, they represent a more general approach to metagenome analysis.

The analysis of MGCs as described herein provides several advantages over the study of individual species of bacteria as they also provide information (e.g. taxonomical and functional information) for unknown/uncharacterised species. Similarly they allow DNA which has not previously been sequenced to be included in the analysis.

SUMMARY OF THE INVENTION

The invention herein relates to methods and products to better identify if a person is at risk or have developed Type 2 diabetes (T2D).

A primary object of the invention is to analyze the microbiota composition, including the presence of specific bacterial genera, species or metagenomic clusters (MGCs) in the gastro intestinal tract of a person to be used alone, or in combination with other measurements such as Body Mass Index (BMI), waist-to-hip ratio (WHR), waist circumference (WC) and specific markers, to better predict whether an individual is at risk for developing type 2 diabetes.

Gut microbial markers have been associated to T2D. However, the problem we have found is that the predictability of using specific biomarkers differs with several factors including between races and age. Our solution is to use different markers for different groups of people and a suitable method in order to identify persons, within such groups, at risk for developing T2D. The invention herein both describes a model we have developed based on especially metagenomic cluster scores that can identify T2D patients. The model has been shown to be able to identify the risk groups with 80% accuracy or, put another way, with an area under the ROC curve (ROC AUC) of up to or greater than 0.83. There are also methods for how the model can be applied for a certain population.

Thus, a method is disclosed for identifying an individual having or at risk of T2D, comprising obtaining a gastro intestinal sample from said individual, for example a fecal sample representing the gastro intestinal ecosystem, and determining the amount of specific microbial genera, species or metagenomic clusters in the sample of said individual.

It is a further object of the invention to provide methods, kits, systems and products for said identification.

Other objects and advantages of the present invention will become obvious to the reader and it is intended that these objects and advantages are within the scope of the present invention.

DETAILED DESCRIPTION OF THE INVENTION AND PREFERRED EMBODIMENTS THEREOF

Figure 1A:
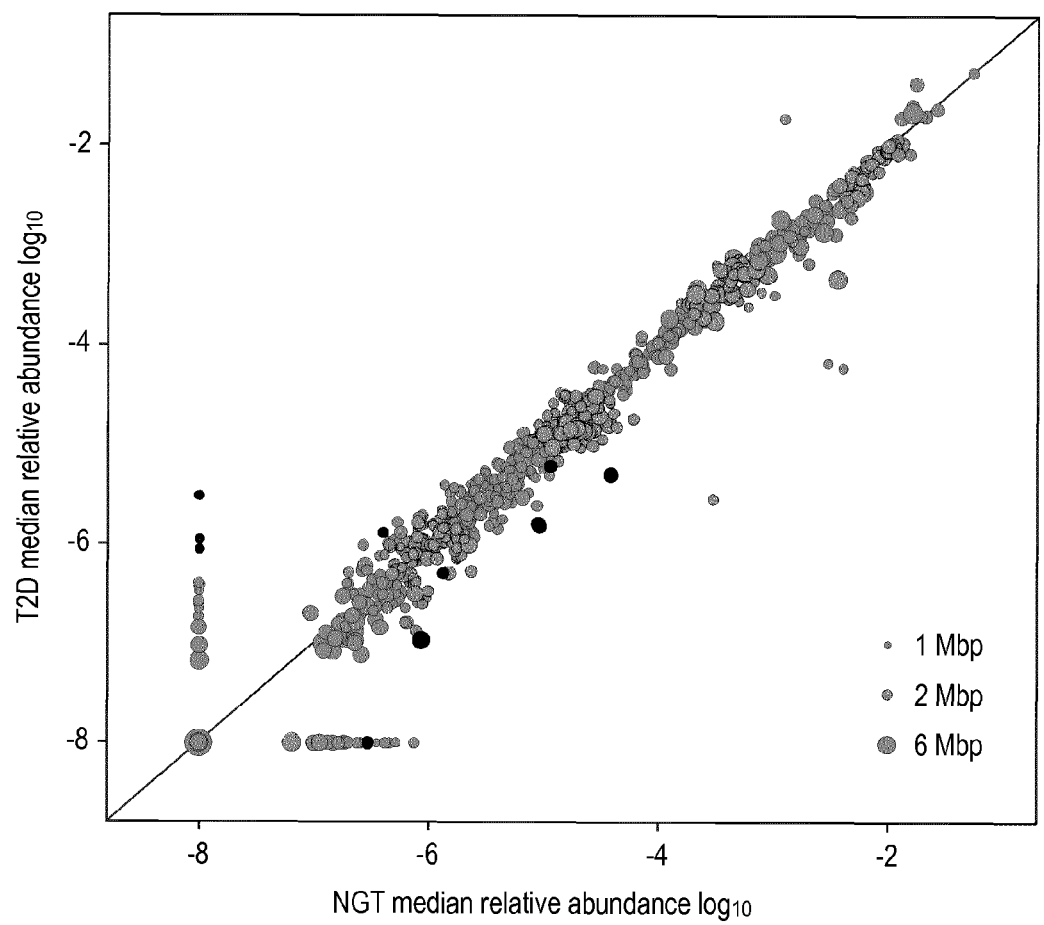
FIG. 1: Species abundance is associated with diabetes and clinical biomarkers but not with enterotype status. a, Scatter plot of median species abundance in T2D and NGT subjects. Grey points represent a species not differentially abundant between groups whereas black points represent species differentially abundant (Adj. P<0.05). b, Principal component analysis of genus abundance with enterotype classification as instrumental variable. Individuals cluster into four groups, with strongest support by the Calinski-Harabasz index (data not shown). NGT subjects are represented by filled circles, IGT subjects are represented by open circles and T2D subjects are represented by open triangles. c, Spearman's rank correlation of clinical data and species abundance. + Adj. P<0.05; * Adj. P<0.01; # Adj. P<0.001.

The gut microbiota has been proposed as an environmental factor that affects body metabolism and insulin sensitivity and has also been found to be altered in obesity. In addition, gut microbial markers have recently been associated to T2D in the metagenomic study of Chinese diabetic patients recently published by Qin et al. (Nature, Sep. 26, 2012). However, the problem we have found is that such markers differ between races/ethnic groups, geographical locations of people (for example meaning various environmental factors including food habits) and age. Our solution is to use different markers for different groups of people in order to identify persons within such groups at risk for developing T2D. The invention herein is based on our finding that for example race and age groups are advantageously separated in the analysis for improved predictability. We have developed a model based on metagenomic cluster analysis/metagenomic cluster score that can identify T2D patients with 80% or greater accuracy or, put another way, with an area under the ROC curve (ROC AUC) of up to or greater than 0.83. This model/score can also separate IGT subjects into those with and without dyslipidemia and high C-peptide levels, thus indicating that the metagenomic score mirrors metabolic mechanisms relevant to the development of T2D.

Qin et al., 2012, supra, does not disclose the concept of MGCs as described herein. In addition, the advantage obtained by analysis of different markers (here MGCs or bacterial species) for different population groups and the fact that the markers might be different between such groups was not disclosed or suggested in Qin et al., 2012, supra., and has been recognised by the present inventors based on their studies.

For example, the population studied in Qin et al., 2012 is a Chinese population and when the Chinese metagenomic data was analysed using the model of the present invention, the Chinese and European populations (i.e. the population studied in the Examples of the present invention) showed that although there were some similarities, overall there were different abundances of bacterial species and MGCs in the two populations (see FIGS. 4 to 8). The MGCs identified for the Chinese cohort in accordance with the present invention were used in the model of the present invention in order to classify the Chinese subjects into T2D and control subjects. An AUC of 0.82 was observed which is in line with the results obtained with the European cohort described herein. However, importantly, the most discriminatory MGCs (and species) differed between the Chinese subjects and the European cohort (FIGS. 3b, 3c, 9a, 9b), thereby showing that it is advantageous and sometimes necessary to use different MGCs (and species) to analyse for T2D in different population groups.

Further support for this was obtained when it was tested whether an MGC model trained on one population could be used to classify T2D individuals from the other population. The MGC model based on the European cohort as described herein had an AUC of 0.58 for the classification of Chinese T2D subjects, whereas the model based on the Chinese cohort had an AUC of 0.66 for the classification of the European T2D subjects. These AUC values are much lower than the values of 0.82 and 0.83 when the MGCs specific for and derived from the particular population were used.

Thus, the work by the present inventors to show that different populations have differences in discriminatory metagenomic markers means that for T2D metagenomic predictive tools, the use of different markers for different populations under investigation is advantageous, e.g. in terms of accuracy. Put another way, the predictive metagenomic tools and markers for T2D (e.g. MGCs as described herein) should be specific for the population under investigation.

Thus, the present invention provides a model to identify an individual having or at risk of developing type 2 diabetes (T2D) using metagenomic clusters (MGCs), wherein said model is characterised by using different metagenomic clusters for different population groups.

The model of the invention can also be regarded as a statistical model, a mathematical model, or an algorithm, and methods of generating models of metagenomic data for use in identifying an individual having or at risk of developing type 2 diabetes (T2D) are also provided. Preferably said models and methods are computer implemented.

A preferred model is based on an analysis of MGCs for example in the form of an MGC score. However, for all the embodiments of the invention, the model and methods etc., may equally be carried out based on an analysis of bacterial species as opposed to an analysis of MGCs.

The population groups of the invention may be any convenient sub-population of individuals and exemplary in this regard are age, geographical location, race/ethnic group, environmental factors such as food habits, and gender, or combinations thereof. Especially preferred population groups are based on age, or geographical location, or age combined with geographical location, or age combined with race/ethnic group, or age combined with geographical location and race/ethnic group. Although the population groups will contain individuals suffering from T2D, the population groups used in the present invention are general and representative of the population groups as a whole and thus will also contain healthy individuals.

Appropriate population groups (sub-populations) based on age can be selected appropriately by a person skilled in the art. For example, relevant population groups may be relatively young groups, such as those aged 20 to 39 or 20 to 44 (or for example 20 to 40, 41, 42 or 43). Other relevant population groups are middle aged groups, such as those aged 40 to 59 or 45 to 64 (or for example 40 or 45 to 59, 60, 61, 62, 63 or 64). Other relevant population groups are older groups, such as those aged 60 to 79, 65 to 79, or 60 and over (at least 60) or 65 and over (at least 65). For the present invention, preferred population groups are aged 60 and over, 65 and over, 68 and over, 70 and over, or 75 and over (at least 60, 65, 68, 70 or 75). Alternatively, closed ended ranges may be selected such as population groups aged 60 or 65 to 90 (or 89), 60 or 65 to 85 (or 84), 60 or 65 to 80 (or 79), 60 or 65 to 75 (or 74). The groups 65 and over and 65 to 90 (or 89), 65 to 85 (or 84), 65 to 80 (or 79), or 65 to 75 (or 74) are preferred. Alternatively preferred populations are older than 60 or 65, etc., optionally with the upper age limits as set out above.

Appropriate population groups (sub-populations) based on geographical location can conveniently be selected at a country level (e.g. China, United States of America, etc.,) or at a continent level (e.g. Asia, Oceania, The Americas, Europe and Africa) or sub-level (e.g. Northern, Southern, Eastern, Western or Central continents). Non-limiting examples might be China (or Asia in general) or Europe (e.g. Northern or Southern Europe), etc.

Appropriate population groups (sub-populations) can also be selected based on race/ethnicity/ethnic group. For example, the population of the specific study described herein are all from the Caucasian race. However, any other race/ethnicity/ethnic group can be selected as a population group (sub-population) for use in the present invention.

Appropriate population groups (sub-populations) can also be selected based on environmental factors. Exemplary environmental factors include, but are not limited to, food habits, e.g. high or low salt, high or low sugar, high or low fat, high or low fibre, food intake or diets.

Appropriate population groups (sub-populations) can also be selected based on gender, e.g. can be male subpopulations (men) or female subpopulations (women). A population group selected based on gender forms a preferred embodiment of the invention. The exemplified population group and a preferred population group in some embodiments consists of females/women.

Appropriate population groups (sub-populations) can also be selected based on a combination of two or more of the above groups. For example, preferred population groups are based on age combined with geographical location, or age combined with race, or age combined with geographical location and race. Other preferred population groups are aged 65 and over, more preferably European or Caucasian populations of age 65 and over, most preferably European Caucasian populations of age 65 and over. Populations of age 68 and over are also preferred. Optionally all the above preferred groups are also characterised by being selected according to gender, e.g. are female/women.

A preferred and exemplified population (sub-population) for the present invention is European Caucasian women of age 65 and over or 68 and over.

Another preferred population (sub-population) is an Asian population aged 40 to 59 (or an alternative middle aged population as given above).

Another preferred population (sub-population) is a European population aged 60 to 79 (or an alternative older population as given above).

Another preferred population (sub-population) is an American (e.g. U.S.A) population aged 45 to 64 (or an alternative middle aged population as given above) or aged 20 to 44 (or an alternative relatively young population as given above).

Analysis of Biomarkers for Input in Predictive Model

For each population group to be studied one or more of the following analysis are made to generate data to be used in the model below to determine a person's (being part of such population) risk for developing T2D or associated metabolic conditions or diseases.

Metagenomic Clusters to Study Gut Microbiota in T2D

To identify microbial species independently of reference genomes and fully exploit the information contained in the metagenomic data, one can perform a de novo assembly of filtered sequence data, first for each individual separately and then using all unassembled reads in one additional assembly to identify also rare genes. The total length of the assembly is recorded and also the number of genes that could be predicted with a length longer than for example 100 bp. Genes are clustered often based on 95% sequence similarity to create a non-redundant gene catalogue, resulting in a number of microbial genes in the population.

These genes and for example the MetaHIT genes (17) may be combined into a new gene catalogue, to align reads. Assuming that genes belonging to one microbial species would co-occur in samples where that species is found, we analyzed the co-occurrence of genes present in at least 10 individuals (2.9 million genes) by calculating the correlation coefficient and then clustering sets of genes with high correlation among them (Pearson rho>0.85). We defined these sets of highly correlated genes as metagenomic clusters (MGCs)

To determine the phylogenetic origin of the MGCs, the genes in each cluster is blasted against the NCBI nr catalogue and the lowest common ancestor (LCA) is determined by requiring that normally at least 50% of the genes have a best hit to the same phylogenetic group. Then is the abundance of the largest MGCs (for example n=800) tested in known NGT and T2D samples to find a certain number of clusters to be differentially abundant between the two groups (Adj. P<0.05).

Gut Microbiota Species Composition in T2D

To characterize the composition of the gut microbiota associated with T2D, the fecal microbiota of the selected population is analyzed. The cohort is selected with a stratified randomized method from a population-based screening sample (12, 13), resulting in subgroups: persons who have T2D, IGT or are healthy (normal glucose tolerance, NGT). Genomic DNA is extracted with a standard procedure (14) and sequenced, preferably on Illumina HiSeq 2000.

To determine the composition of the gut microbiota, the filtered Illumina reads are aligned to multiple non-redundant reference genomes obtained from for example the NCBI and HMP databases (hmpdacc.org). The most abundant genera, species and genomes in the cohort are calculated and compared between the subgroups.

T2D Status can be Discriminated by the Microbiota

To use the microbiota composition to identify diabetes status a Random Forest (RF) model (Breiman, Leo (2001). "Random Forests". *Machine Learning* 45 (1): 5-32. doi:10) or similar model needs to be trained in a test set of the NGT and T2D subjects. Its performance is evaluated on unseen samples from the same groups and the predictive power is scored in a receiver operator characteristic (ROC) analysis.

Using the data from the metagenomic clusters from above and possibly also the data from the gut microbiota species composition, also from above, the RF model generates a variable importance score for each species and MGC representing the predictive power. The importance score is used to rank species and MGCs, and the top most important ones are used in the model for predicting T2D.

The discriminatory power of species and MGCs are calculated as the area under the ROC curve (AUC).

Thus, the present invention further provides a model to identify an individual having or at risk of developing type 2 diabetes (T2D) using metagenomic clusters (MGCs) as described herein wherein said model is characterised by using different MGCs for different population groups as described herein, wherein construction of the model comprises: (i) selecting the population group to be studied; (ii) obtaining gut metagenomic sequence data from said population; and (iii) identifying MGCs from all the metagenomic sequence data from said population.

Steps (i) to (iii) may be repeated for each different population group selected which can give rise to different MGCs for different population groups.

The same steps can equally be carried out based on the identification and analysis of bacterial species as opposed to MGCs.

Once MGCs (or species) have been identified in accordance with the invention then known normal and T2D samples from the relevant population group can be analysed or tested in order to determine which MGCs (or species) are differentially abundant between the two groups (i.e. between normal and T2D samples). An appropriate and preferred way to do this is to use a random forest (or similar) model, for example as described above.

Thus, a yet further embodiment of the present invention provides a model as described herein wherein (a) a random forest or similar model is used to train on a test set of normal and T2D samples to generate a predictive model for T2D; (b) using or generating a list of importance scores of the MGCs in the model; and (c) using the top scoring MGCs in the model for predicting T2D.

The same steps can equally be carried out based on the identification and analysis of bacterial species as opposed to MGCs.

Figure 3A:
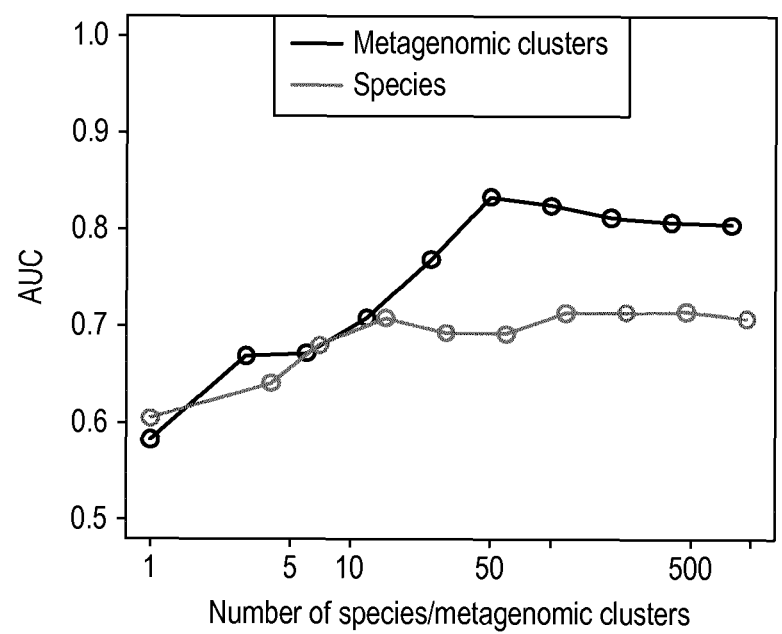
FIG. 3: Classification of diabetes status by abundance of species and MGCs. a, Classification performance of a random forest model using species or MGC abundance assessed by area under the receiver-operating characteristic curve (AUC). The performance was explored for different numbers of explanatory variables, ordered in importance. The lower line shows the results obtained with species and the upper line shows the results obtained with MGCs. b, 30 most important MGCs in the predictive model using all 800 MGCs and discriminating NGT and T2D subjects. Bar length indicates the importance of the variable and colors represent enrichment in T2D (red shades, marked 'r') or in NGT (blue shades, marked 'b'). c, 30 most important species in the predictive model using 915 species and discriminating NGT and T2D subjects. Bar length indicates the importance of the variable and colors represent enrichment in T2D (red shades, marked 'r') or in NGT (blue shades, marked 'b'). d, Use of the model trained for discriminating NGT and T2D with MGC to predict the probability of IGT subjects being either NGT (light circles in bottom part of figure below the line) or T2D (darker circles in top part of figure above the line). e, IGT subjects predicted to be T2D (right hand column) had higher triglyceride concentration (Mann-Whitney U-test p=0.019). f, IGT subjects predicted to be T2D (right hand column) had higher C-peptide levels (Mann-Whitney U-test p=0.03).
Figure 3C:
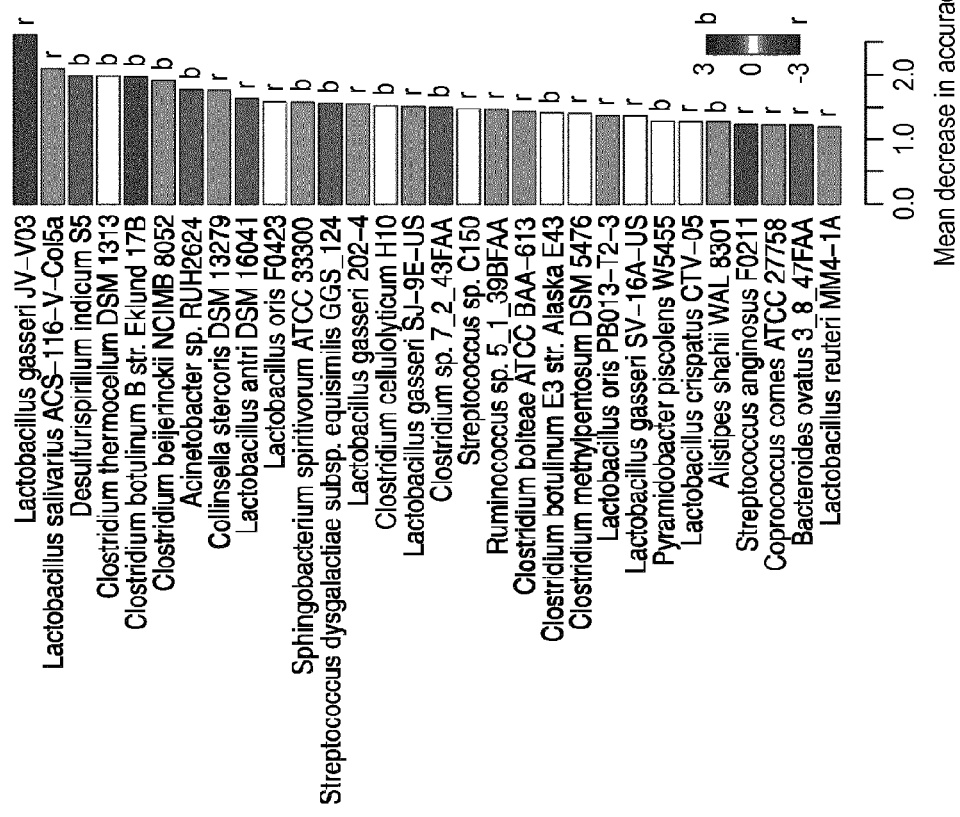
Figure 3B:
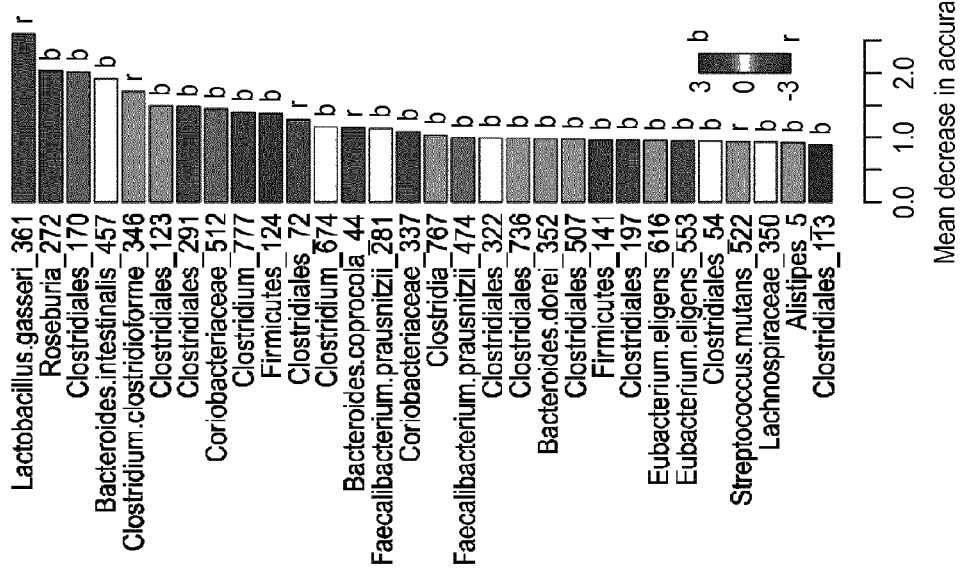

The top scoring MGCs or species are the ones which are the most discriminant between normal and T2D samples (see e.g. FIGS. 3b and 3c).

These steps may be repeated for each different population group studied which can give rise to different MGCs (or species) for different population groups.

The appropriate number of top scoring MGCs (or species) to be used in the models of the invention for predicting T2D can readily be determined by a person skilled person in the art and would be chosen such that the predictive model for T2D could identify T2D patients with a desired level of accuracy or predictive power. Predictive power is preferably measured by ROC AUC in which case a desired level of predictive power would be a ROC AUC value of at or about 0.60 or greater, at or about 0.65 or greater, at or about 0.70 or greater, at or about 0.75 or greater, or at or about 0.80 or greater. Alternatively such ROC AUC values would be from at or about 0.60 or greater to at or about 0.80 or greater, more preferably from at or about 0.65 or 0.70 or greater to at or about 0.80 or greater (e.g. when MGCs are analysed) or a ROC AUC value of from at or about 0.60 or 0.65 or greater to at or about 0.70 or 0.75 or greater (e.g. where the analysis is at the species level).

Alternatively, preferred levels of accuracy would be at or about 60% to at or about 80% or greater, more preferably at or about 70% to at or about 80% or greater (e.g. when MGCs are analysed) or at or about 60% to at or about 70% or greater (e.g. where analysis is at the species level), or other equivalent values to the ROC AUC values given above.

A convenient way of assessing the appropriate number of MGCs (or species) to use is illustrated in FIG. 3a (and Table 3) where the AUC value is plotted for various numbers of the top scoring MGCs or species and it can be seen that for the particular exemplified population the highest AUC value (0.83) is obtained when the top 50 MGCs are used or the top 238 species are used (AUC=0.71). Thus, the appropriate number of MGCs (or species) to use in the models and methods of the invention can readily be assessed to achieve an appropriate and desired AUC value (or % accuracy). As evidenced in the Examples, the composition of the microbiota as determined by MGCs in accordance with the present invention correlates better with T2D than the known risk factors of BMI (AUC=0.58), WHR (AUC=0.60) and WC (AUC=0.70). Importantly, the T2D score obtained based on MGCs is similar to other published scores that combine several known risk factors for diabetes development (e.g. the FINDRISC score, validated in several countries (7)).

MGCs (as described herein) for each selected population group can be identified by any appropriate method. However, in preferred embodiments of the invention the MGCs for each of said population groups are provided by:
(i) performing a de novo assembly of sequence data (e.g. filtered sequence data) from the gut metagenome, first for each individual of the population separately and then using all unassembled reads in one additional assembly to identify also rare genes;
(ii) clustering genes based on sequence similarity to create a non-redundant gene catalogue resulting in a number of microbial genes in the population;
(iii) analysing the co-occurrence of genes present in at least 2 individuals by calculating the correlation coefficient across subjects and then clustering sets of genes with high correlation among them to provide MGCs.

In alternative embodiments, step (iii) can be carried out based on a co-occurrence in at least 5, 10 or 20 individuals. In preferred embodiments the sequence similarity in step (ii) is 95% and/or the high correlation in step (iii) is a Pearson rho value of >0.85. In other alternative embodiments metagenomic sequence data other than gut data (e.g. sequence data from an oral metagenomic sample) can be used.

In preferred embodiments of the above, MGCs are studied.

In the context of T2D, appropriate normal subjects/normal samples are those from individuals with NGT (i.e. with normal glucose tolerance), also referred to herein as healthy or control individuals or subjects.

The models of the invention may be used in combination with any other appropriate measurement or risk factor relevant to the identification of T2D. Exemplary other measurements are body mass index (BMI), waist-to-hip ratio (WHR) and/or waist circumference. Other potential risk factors include age, family history, diet, sedentary lifestyle or obesity and one or more of these may also be measured. In addition, other specific biomarkers shown to be associated with T2D can be measured or analysed in combination with the models and methods of the present invention.

The metagenomic sequence data for use in the present invention can be derived or obtained from any appropriate source. For example, appropriate metagenome containing samples from a population group can be obtained, e.g. faecal (appropriate for gut metagenome) or oral samples, after which genomic DNA can be extracted, sequenced, and analysed by known sequence techniques and tools such as for example whole genome sequencing, e.g. whole genome shotgun sequencing. Alternatively appropriate metagenomic sequence data may already be available for analysis, for example in the form of an existing sequence database such as the MetaHIT genes described elsewhere herein or from the cohorts described in Qin et al, 2012.

"filtered sequence data" as referred to herein would be understood by a person skilled in the art and can be obtained by any appropriate means which would be well known to a person skilled in the art. Such filtration is used to clean up the initial sequence data with the aim that it should include only metagenomic sequences (for example by removing any non-metagenomic sequences, or removing as many non-metagenomic sequences as possible), for example by removing any human sequences which are present.

As outlined above, the present invention also provides methods of generating models of the present invention, for example methods of generating a model of metagenomic data for use in identifying an individual having or at risk of developing type 2 diabetes (T2D). A preferred such method comprises:
(i) selecting a population group to be studied, wherein said population group is as defined elsewhere herein, but preferably is based on age or gender, optionally in combination with one or more of geographical location, race/ethnic group, and environmental factors such as food habits;
(ii) obtaining gut metagenomic sequence data from said population; and
(iii) identifying metagenomic clusters from all the metagenomic sequence data from said population.

Other preferred features of the methods are described elsewhere herein in connection with the models of the invention.

Other embodiments of the invention can be practiced for example by using other sequencing techniques to analyse the microbial composition of the gastro intestinal microbiota, alone or in combination with other analysis.

The invention can also be practised using other methods for quantification of specific species or groups known in the art. These methods include, but are not limited to, quantitative PCR, ELISA, microarrays etc.

The present invention is readily used in a clinical setting to aid in the assessment of whether a person is in a risk group for developing T2D (see also Example 7). In such a setting, an appropriate sample, e.g. a faecal sample, is provided by the patient, after which said sample is processed as described herein and a metagenomic analysis is undertaken as described herein, for example to determine or measure a MGC score. The person is assigned to an NGT (healthy/normal) or T2D risk group by applying the predictive model for NGT or T2D as described herein. This alone or in combination with customary clinically used risk values for the other variables, such as BMI and WC can be used to determine if the person is at risk for developing T2D and should be further investigated, monitored or treated. Assignation or classification to the T2D group indicates that the individual has or is at risk of developing T2D and for example requires further investigation, monitoring or treatment.

Thus, a further aspect of the present invention provides the use of the model or method of the invention in a method of identifying an individual having or at risk of having or suspected of having/developing T2D said use comprising obtaining a gut microbial sample from said individual and using the model or method of the invention to determine or measure (from the sample) whether the individual has or is at risk of developing T2D.

A yet further aspect provides a method for identifying an individual having or at risk of having or suspected of having/developing T2D, comprising obtaining a gut microbial sample from said individual and using the model or method of the invention to determine or measure (from the sample) whether the individual has or is at risk of developing T2D. Such methods may also be referred to as diagnostic methods.

Figure 3D:
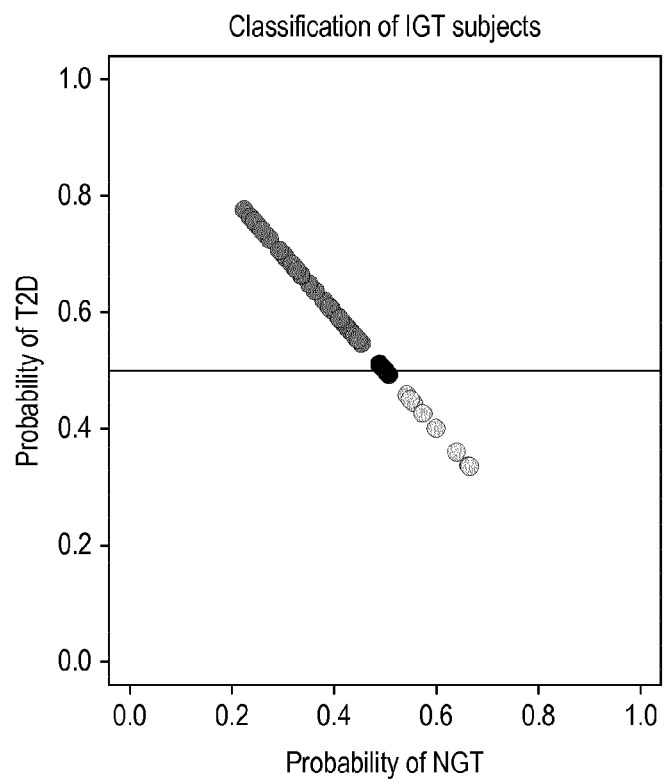

Conveniently, in such methods, an individual is assigned to a normal group or to a T2D group by applying the predictive model or method of the invention, wherein assignation to the T2D group indicates that the individual has or is at risk of developing T2D. The use of the invention to carry out such assignation or stratification or classification of patients is for example shown in FIG. 3d and described in the Examples. For example, a probability value of above (preferably significantly above) 0.5 for either T2D or normal (NGT) means that the individuals can be classified (see FIG. 3d).

The present invention further provides a method for identifying an individual having or at risk of having or suspected of having/developing T2D comprising obtaining a gut microbial sample from said individual and determining the levels or abundance in said sample of at least the top 5, 10, 15, 20, 25 or 30 of the most predictive MGCs or bacterial species identified by the methods or models of the present invention. It should be noted that once the most predictive MGCs have been identified then the bacterial species (or in some cases orders) corresponding to these can readily be identified (e.g. by using reference genomes such as those at NCBI). Such bacterial species (and orders) are indicated in FIG. 3b and it can be noted that they are different from the species identified in FIG. 3c (i.e. in the analysis not involving the use of MGCs) and these species can conveniently be used for diagnosis of T2D.

Thus, a preferred such method comprises the analysis of the levels or abundance of at least 5, 10, 15, 20, 25 or 30 (e.g. all 30) of the species of the MGCs, or bacterial species, listed in FIG. 3b or 3c, respectively.

The 30 MGCs are *Lactobacillus.gasseri*_361; *Roseburia*_272; *Clostridiales*_170; *Bacteroides.intestinalis*_457; *Clostridium.clostridioforme*_346; *Clostridiales*_123; *Clostridiales*_291; *Coriobacteriaceae*_512; *Clostridium*_777; *Firmicutes*_124; *Clostridiales* 72; *Clostridium*_674; *Bacteroides.coproccola*_44; *Faecalibacterium.prausnitzil*_281; *Coriobacteriaceae*_337; *Clostridia*_767; *Faecalibacterium.prausnitzil*_474; *Clostridiales*_322; *Clostridiales*_736; *Bacteroides.dorei*_352; *Clostridiales*_507; *Firmicutes*_141; *Clostridiales*_197; *Eubacterium.eligens*_616; *Eubacterium.eligens*_553; *Clostridiales*_54; *Streptococcus.mutans*_522; *Lachnospiraceae*_350; *Alistipes*_5; *Clostridiales*_113; and the species or orders corresponding to these are: *Lactobacillus.gasseri*; *Roseburia*; *Clostridiales*; *Bacteroides.intestinalis*; *Clostridium.clostridioforme*; *Coriobacteriaceae*; *Clostridium*; *Firmicutes*; *Bacteroides.coproccola*; *Faecalibacterium.prausnitzil*; *Clostridia*; *Bacteroides.dorei*; *Eubacterium.eligens*; *Streptococcus.mutans*; *Lachnospiraceae*; *Alistipes*.

Thus, preferred methods comprise the analysis of the levels or abundance of at least 5, 10, or 15 (e.g. all 16) of the species and orders corresponding to the MGCs, i.e. the levels or abundance of at least 5, 10, or 15 (e.g. all 16) of *Lactobacillus.gasseri*; *Roseburia*; *Clostridiales*; *Bacteroides.intestinalis*; *Clostridium.clostridioforme*; *Coriobacteriaceae*; *Clostridium*; *Firmicutes*; *Bacteroides.coproccola*; *Faecalibacterium.prausnitzil*; *Clostridia*; *Bacteroides.dorei*; *Eubacterium.eligens*; *Streptococcus.mutans*; *Lachnospiraceae*; and *Alistipes*. Alternatively, the levels or abundance of at least 6, 8, 10, 12 or 13 (or at least 7, 9, 11 or 14) of these species can be analysed.

For example and preferred for the diagnosis of the populations exemplified herein (e.g. for a Caucasian European woman of age 60 or 65 and over, or for a European or Caucasian population, in particular a European and/or Caucasian population of age 60 or 65 and over, which are preferably women), said diagnosis could comprise the analysis of at least the top 5, 10, 15, 20, 25 or 30 (e.g. all 30) of the species (or orders) of the MGCs or bacterial species listed in FIG. 3b or FIG. 3c, respectively. The top 30 MGCs are, in order, *Lactobacillus.gasseri*_361; *Roseburia*_272; *Clostridiales*_170; *Bacteroides.intestinalis*_457; *Clostridium.clostridioforme*_346; *Clostridiales*_123; *Clostridiales*_291; Coriobacteriaceae_512; *Clostridium*_777; *Firmicutes*_124; *Clostridiales*_72; *Clostridium*_674; *Bacteroides.coproccola*_44; *Faecalibacterium.prausnitzil*_281; Coriobacteriaceae_337; *Clostridia*_767; *Faecalibacterium.prausnitzil*_474; *Clostridiales*_322; *Clostridiales*_736; *Bacteroides.dorei*_352; *Clostridiales*_507; *Firmicutes*_141; *Clostridiales*_197; *Eubacterium.eligens*_616; *Eubacterium.eligens*_553; *Clostridiales*_54; *Streptococcus.mutans*_522; Lachnospiraceae_350; *Alistipes*_5; *Clostridiales*_113; and the species (or orders) corresponding to these are, in order: *Lactobacillus.gasseri; Roseburia; Clostridiales; Bacteroides.intestinalis; Clostridium.clostridioforme;* Coriobacteriaceae; *Clostridium; Firmicutes; Bacteroides.coproccola; Faecalibacterium.prausnitzil; Clostridia; Bacteroides.dorei; Eubacterium.eligens; Streptococcus.mutans;* Lachnospiraceae; and *Alistipes*. Alternatively, the levels or abundance of at least the top 6, 8, 10, 12 or 13 of these species can be analysed.

Similarly, for the diagnosis of the populations exemplified herein (e.g. for a Caucasian European woman of age 65 and over, or for a European or Caucasian population, in particular a European and/or Caucasian population of age 60 or 65 and over, which are preferably women) such methods could comprise the analysis of at least the top 5, 10, 15, 20, 25 or 30 (e.g. all 30) of the species listed in FIG. 3c, respectively.

Most preferred species to be analysed in the above diagnostic methods are one or more (and preferably all) of *L. gasseri, Roseburia, Clostridiales, B. intestinalis, C. clostridioforme* and Coriobacteriaceae.

Once the levels or abundance of the species have been analysed as above, it is then determined whether the individual has T2D or is normal (healthy, NGT) by appropriate techniques, e.g. by comparison to levels in samples from patients known to have T2D or from healthy/control individuals. The methods or models of the invention could be used for this assignation/stratification/classification of patients to a normal group or a T2D group. In addition, when the population group is appropriate, information as to the type of correlation associated with various species (i.e. whether or not they are associated with T2D or normal/NGT groups) can be obtained from the information provided in the attached Examples and Figures (for example FIG. 3b or 9b). Indeed, preferred and exemplary species to be analysed can be found in the Examples and Figures.

Any appropriate gut microbial sample could be used in such diagnostic methods. For example, an appropriate biological sample might be a faecal sample or an intestinal sample such as an intestinal biopsy sample, preferably a faecal sample. In some embodiments an oral metagenomic sample might be used.

The diagnostic methods are generally carried out in vitro on biological samples obtained from an appropriate subject.

A further aspect of the invention provides a kit for identifying an individual having or at risk of having T2D, comprising reagents suitable for determining the levels or abundance of the species (or orders) corresponding to the MGCs or the species described above.

Preferred formats of kit (and hence preferred techniques for use in the diagnosis) would be microarrays to enable such determination or a set of appropriate PCR primers (e.g. for quantitative PCR).

In all the models and methods of the invention, unless described differently elsewhere herein, it is preferred that any differences or correlations observed between samples, individuals, groups, etc., are significant, more preferably statistically significant (preferably with a probability value of <0.05). Some preferred and exemplary methods of statistical analysis are referred to in the Examples.

The methods and models of the invention as described herein can be carried out with any type of subject/individual/population group which is capable of suffering from T2D. The models and methods are generally carried out on mammals, preferably humans.

The present invention also encompasses use of the microbiota (which includes the presence of specific bacterial genera, species or metagenomic clusters, MGCs) as a biomarker to construct microbiota profiles. Generally speaking, a microbiota profile is comprised of a plurality of values with each value representing the abundance of a microbiota biomolecule (e.g. an MGC or bacterial species). The abundance of a microbiota biomolecule may be determined, for instance, by sequencing the nucleic acids of the microbiota as detailed in the examples. This sequencing data may then be analyzed by known software.

A profile may be digitally-encoded on a computer-readable medium. The term "computer-readable medium" as used herein refers to any medium that participates in providing instructions to a processor for execution. Such a medium may take many forms, including but not limited to non-volatile media, volatile media, and transmission media. Non-volatile media may include, for example, optical or magnetic disks. Volatile media may include dynamic memory. Transmission media may include coaxial cables, copper wire and fiber optics. Transmission media may also take the form of acoustic, optical, or electromagnetic waves, such as those generated during radio frequency (RF) and infrared (IR) data communications. Common forms of computer-readable media include, for example, a diskette, hard disk, magnetic tape, or other magnetic medium, a CD-ROM, CDRW, DVD, or other optical medium, a RAM, a PROM, and EPROM, a FLASH-EPROM, or other memory chip or cartridge, a carrier wave, or other medium from which a computer can read. A particular profile may be coupled with additional data about that profile on a computer readable medium. For instance, a profile may be coupled with data to analyze if the person is within a risk group, or for intervention; what therapeutics, compounds, or drugs may be efficacious for that profile. Conversely, a profile may be coupled with data about what therapeutics, compounds, or drugs may not be efficacious for that profile.

The microbiota profile from the host may be determined using DNA sequencing according to the invention. The reference profiles may be stored on a computer-readable medium such that software known in the art and detailed in the examples may be used to compare the microbiota profile and the reference profiles.

It is a further object of the invention to provide kits, systems and products for the identifications described herein.

Thus, the present invention further provides software comprising instructions to cause a computer to carry out the model or method of the invention. Alternatively the present invention provides software used to generate the model of the invention.

The present invention further provides a system for use in identifying an individual having or at risk of developing T2D, said system comprising a computer carrying the software of the invention or otherwise programmed to carry out the model or method of the invention.

The present invention further provides a kit for use in identifying an individual having or at risk of developing T2D, said kit comprising a computer-readable medium which digitally encodes microbiota reference profiles (for example comprising MGCs) from population groups as defined elsewhere herein.

Any kits of the invention may further comprise instructions for carrying out the methods of the invention.

The present invention further provides a computer readable medium comprising the software of the invention to carry out the model or method of the invention and/or which comprises digitally encoded microbiota reference profiles (for example comprising MGCs) from population groups as defined elsewhere herein.

The present invention further provides the use of the software, system, kit or computer readable medium as described above, to analyse the microbiota profile of an individual and then to determine whether the individual has or is at risk of developing T2D. Said uses preferably further comprise the step of comparing the microbiota profile of the individual and a microbiota reference profile from population groups as defined elsewhere herein, and then determining whether the individual has or is at risk of developing T2D.

The present invention further provides the use of the software, system or kit as described above to carry out the model or methods of the invention.

The methods herein to determine people with T2D or at risk of developing T2D are used to decide, design and implement suitable treatments or preventative measures to avoid disease and risk for disease.

The following are some examples of the invention, which are not meant to be limiting of the use of the invention herein but to show practical examples to detail how the invention may be used.

Example 1

Test of the Method on a Caucasian Group; 70-Year Old Women in Northern Europe

In the present study we examined the metagenomic composition of the fecal microbiota of 145 Caucasian women from Europe with T2D, impaired or normal glucose tolerance, and sought to identify microbial markers for T2D pathophysiology and risk assessment. As the T2D women of our cohort exhibited varying levels of blood glucose control and treatment (Table 1), we also analyzed the effects of glucose control and medications on the composition of the fecal microbiota. Additionally, we collected extensive biometric and plasma measurements to correlate gut microbiota alterations with pathophysiological disease mechanisms.

Example 2

Gut Microbiota Species Composition in T2D

Figure 4A:
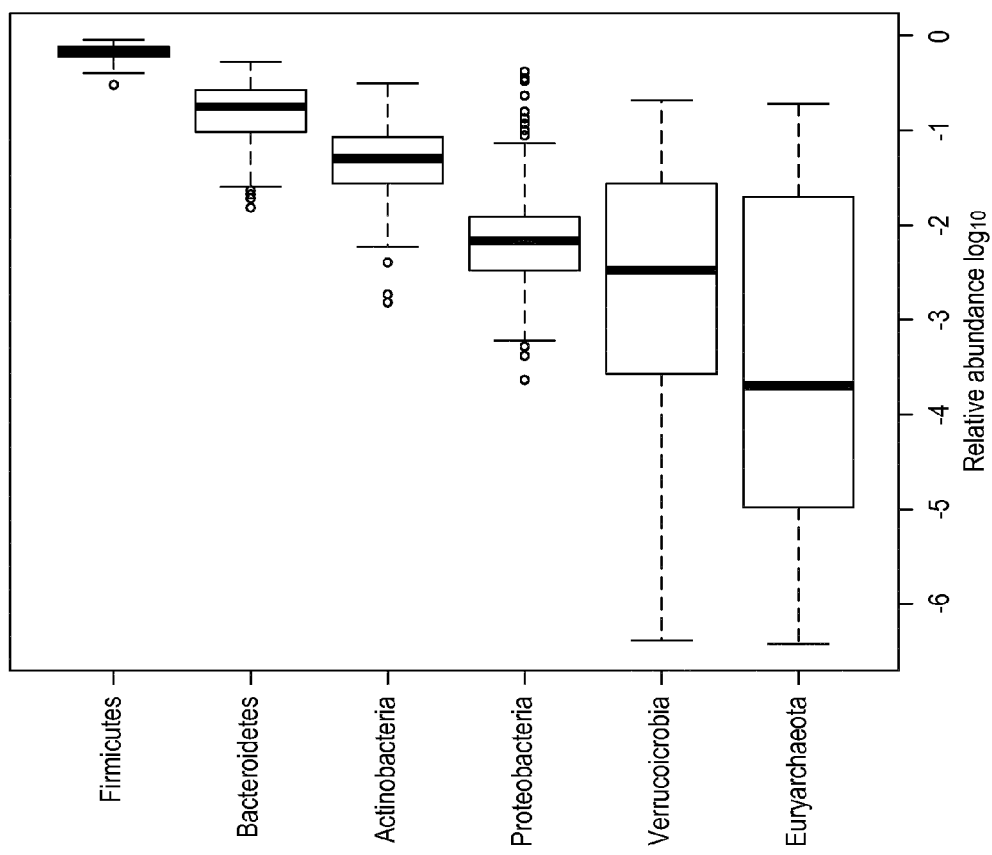
FIG. 4: Relative abundance of bacterial phyla and genera in the studied European cohort. a, 6 most abundant phyla. b, 30 most abundant genera. Boxes denote the interquartile range (IQR) between the first and third quartiles and the line within denotes the median; whiskers denote the lowest and highest values within 1.5 times IQR from the first and third quartiles, respectively. Circles denote data points beyond the whiskers.
Figure 4B:
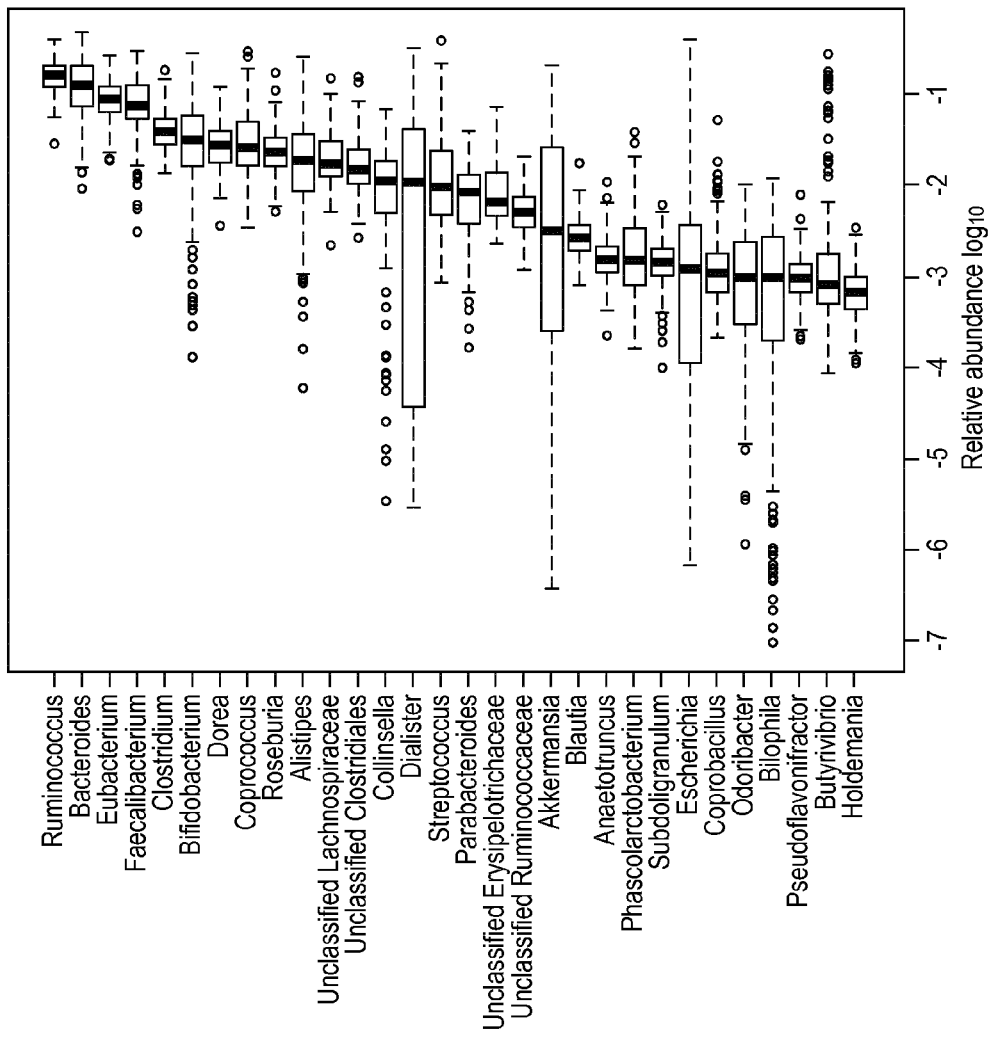
Figure 5A:
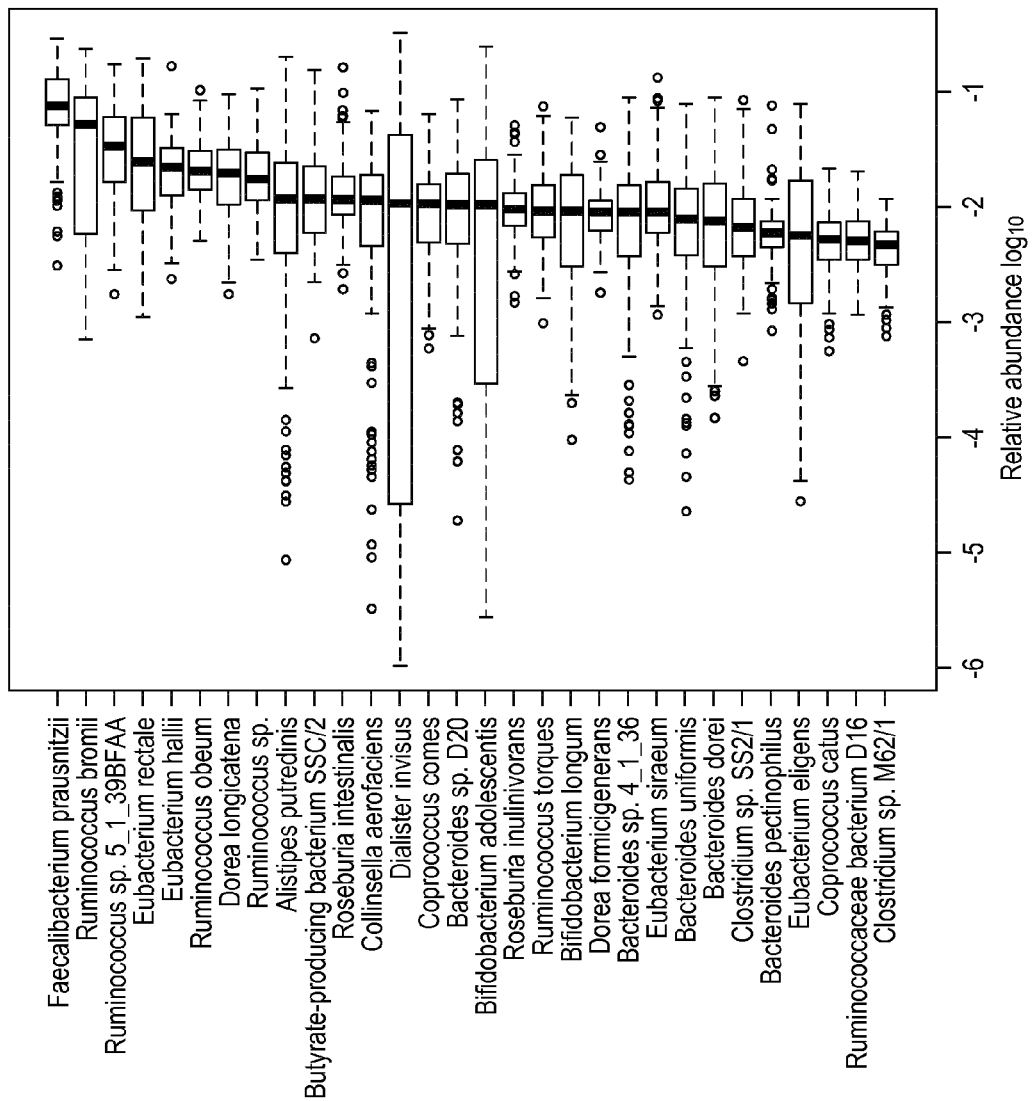
FIG. 5: Relative abundance of bacterial species and genomes in the studied European cohort. a, 30 most abundant species. b, 30 most abundant genomes. Boxes denote the interquartile range (IQR) between the first and third quartiles and the line within denotes the median; whiskers denote the lowest and highest values within 1.5 times IQR from the first and third quartiles, respectively. Circles denote data points beyond the whiskers.
Figure 5B:
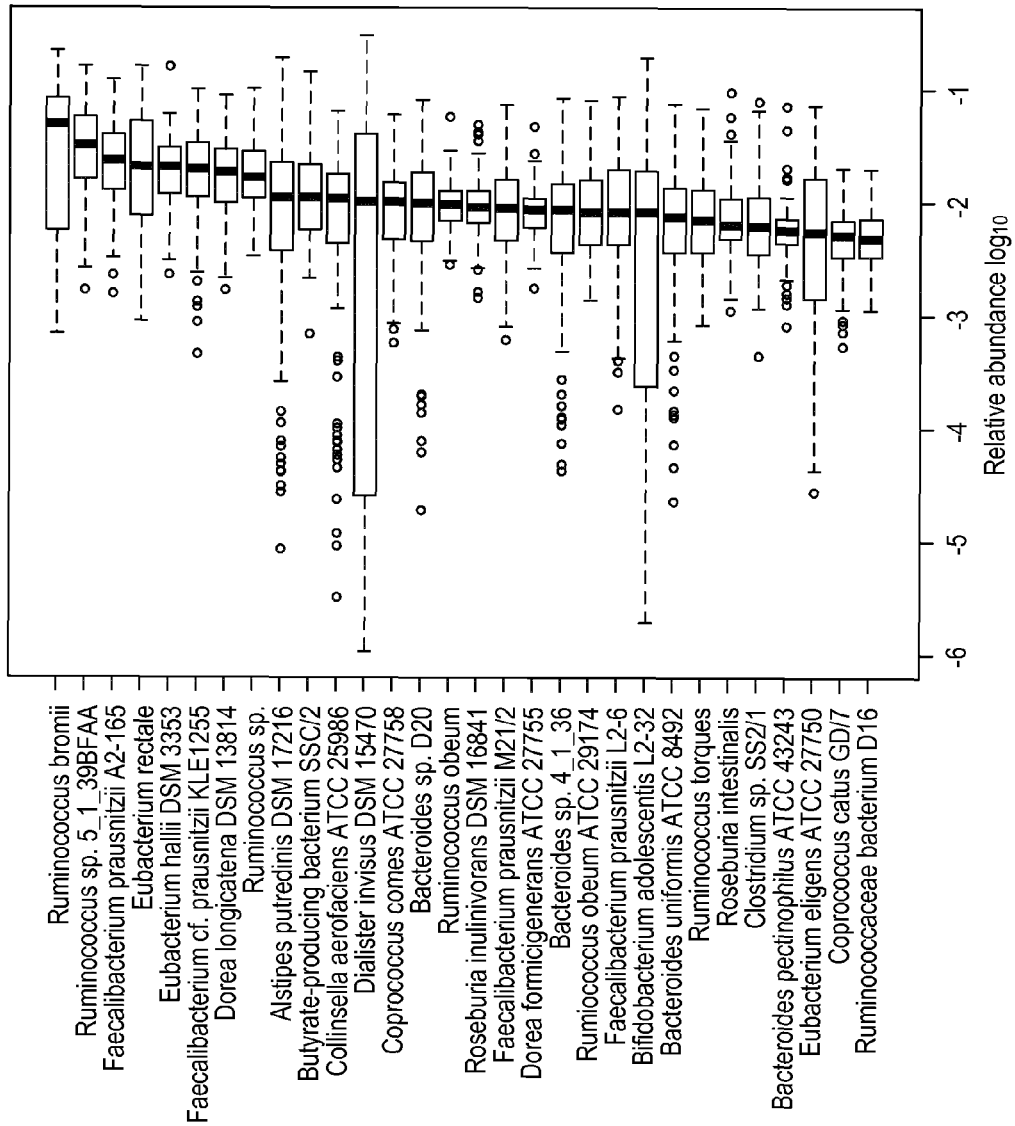
Figure 6A:
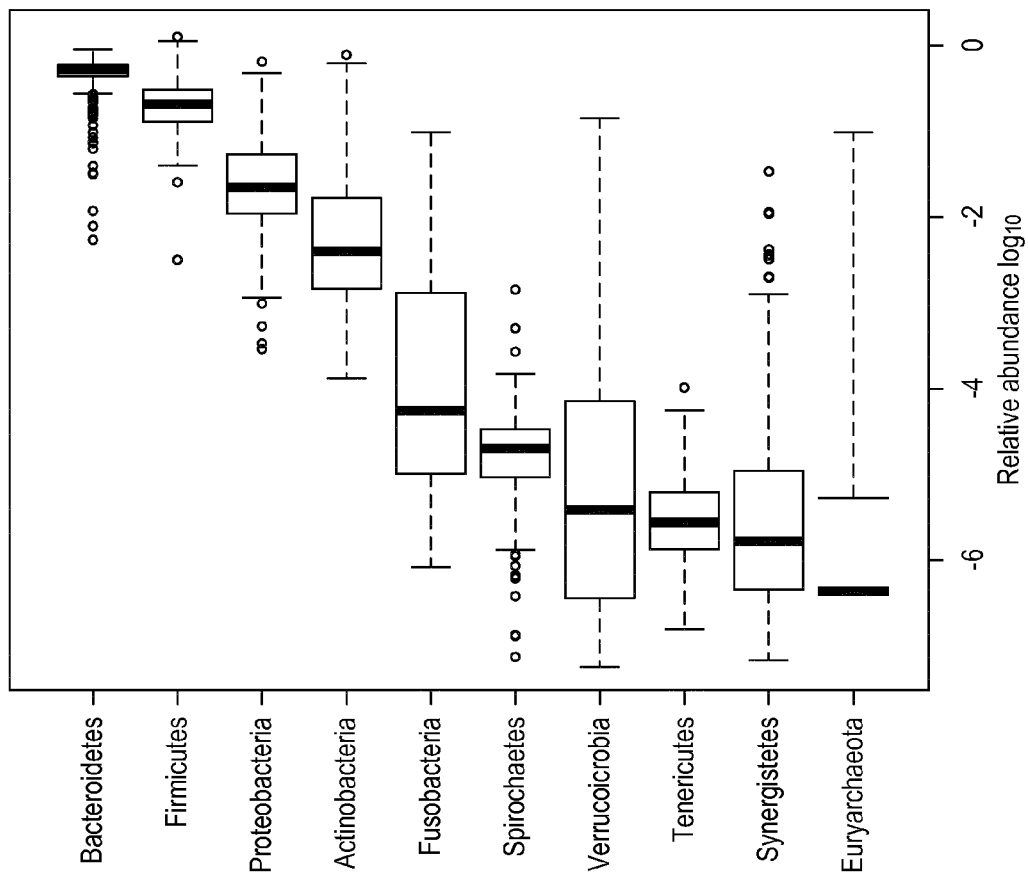
FIG. 6: Relative abundance of bacterial phyla and genera in Chinese metagenomes. a, 10 most abundant phyla. b, 30 most abundant genera. Boxes denote the interquartile range (IQR) between the first and third quartiles and the line within denotes the median; whiskers denote the lowest and highest values within 1.5 times IQR from the first and third quartiles, respectively. Circles denote data points beyond the whiskers.
Figure 6B:
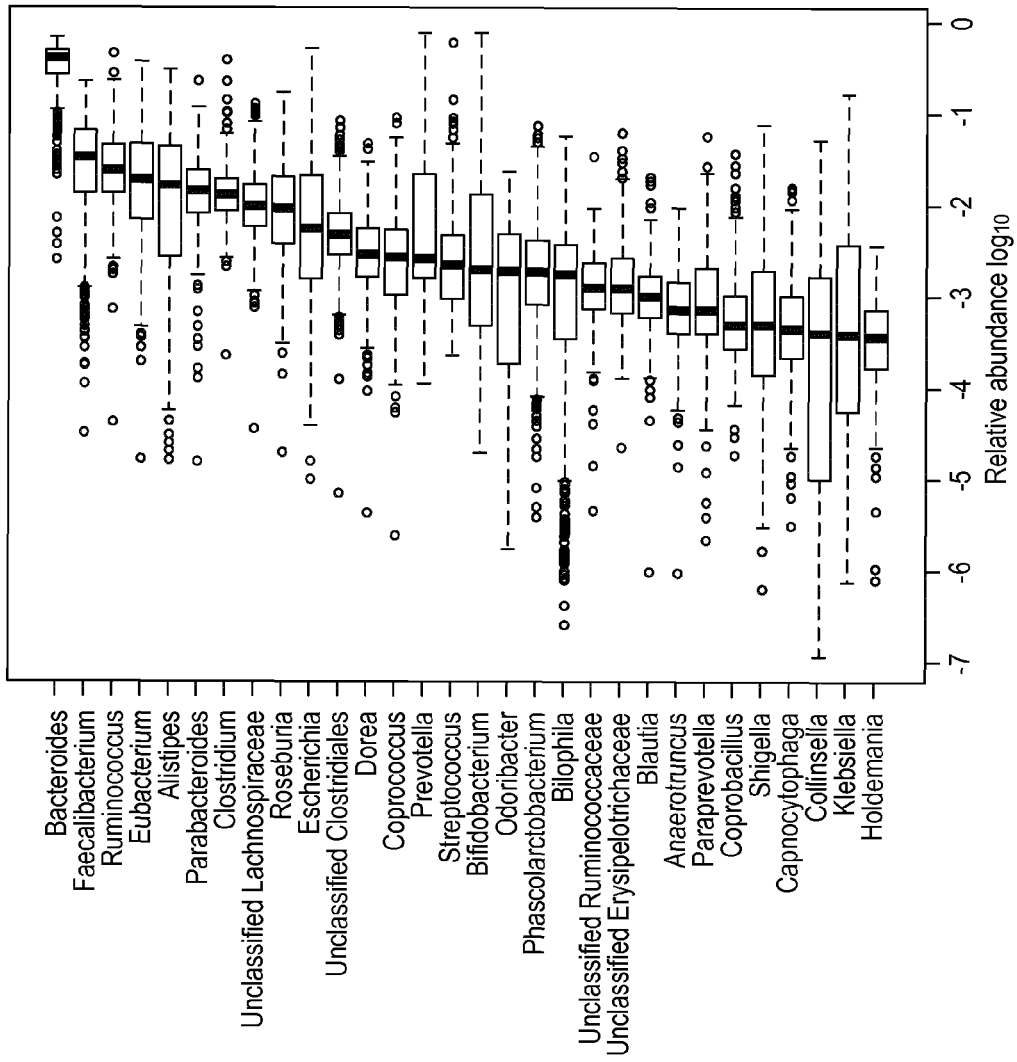
Figure 7A:
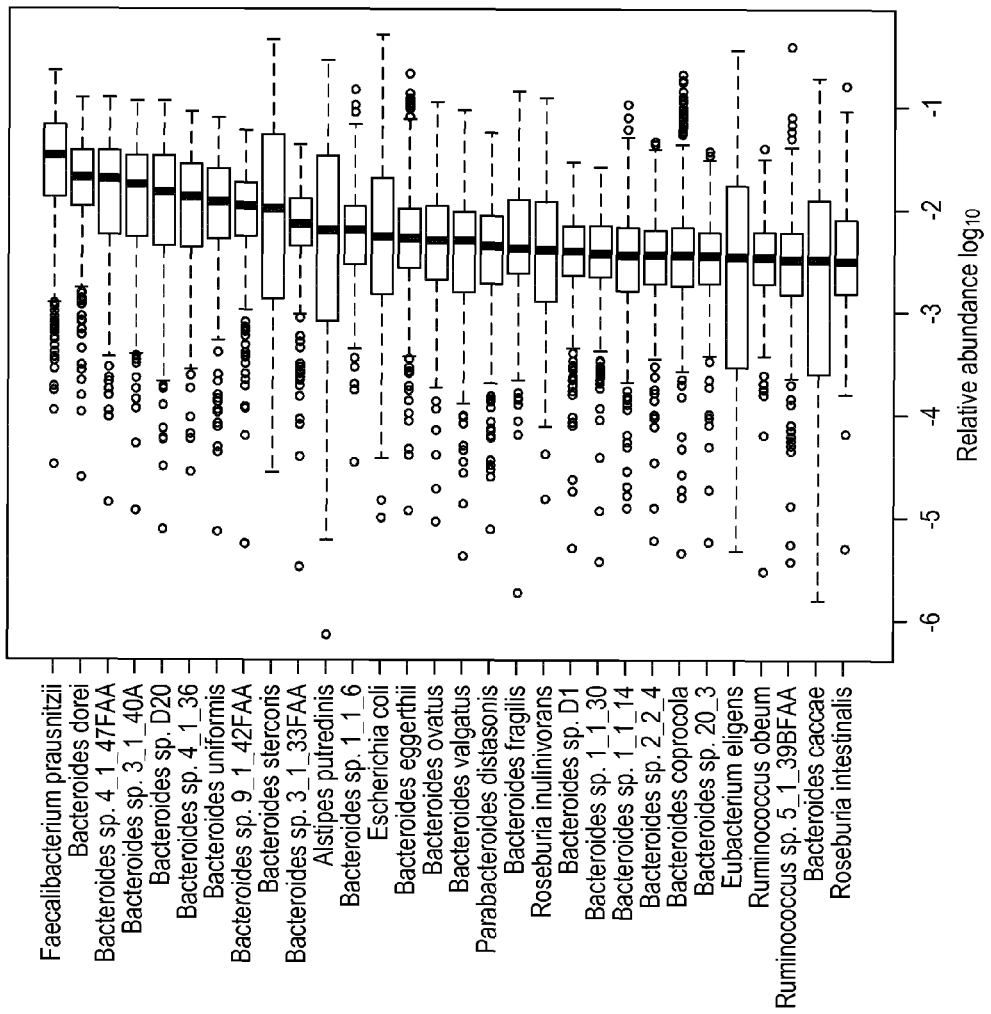
FIG. 7: Relative abundance of bacterial species and genomes in Chinese metagenomes. a, 30 most abundant species. b, 30 most abundant genomes. Boxes denote the interquartile range (IQR) between the first and third quartiles and the line within denotes the median; whiskers denote the lowest and highest values within 1.5 times IQR from the first and third quartiles, respectively. Circles denote data points beyond the whiskers.
Figure 7B:
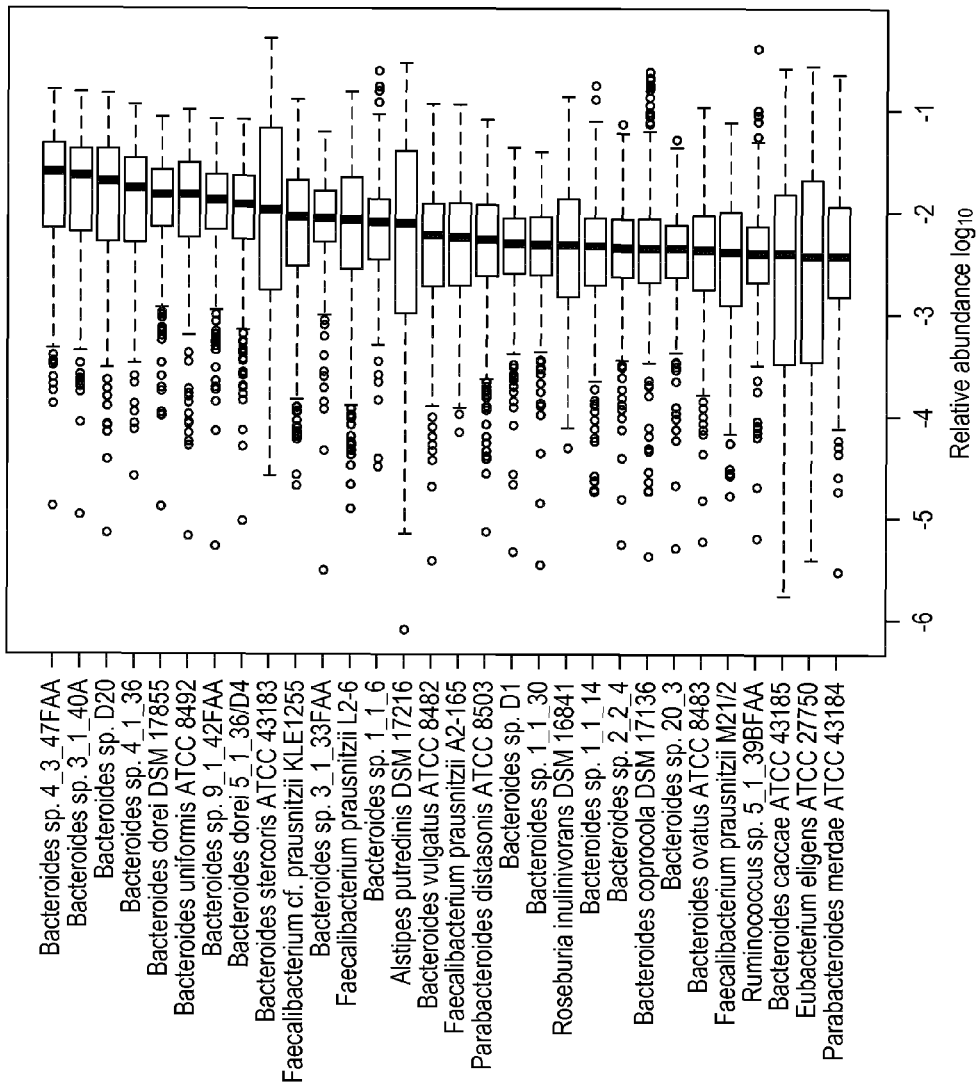
Figure 8A:
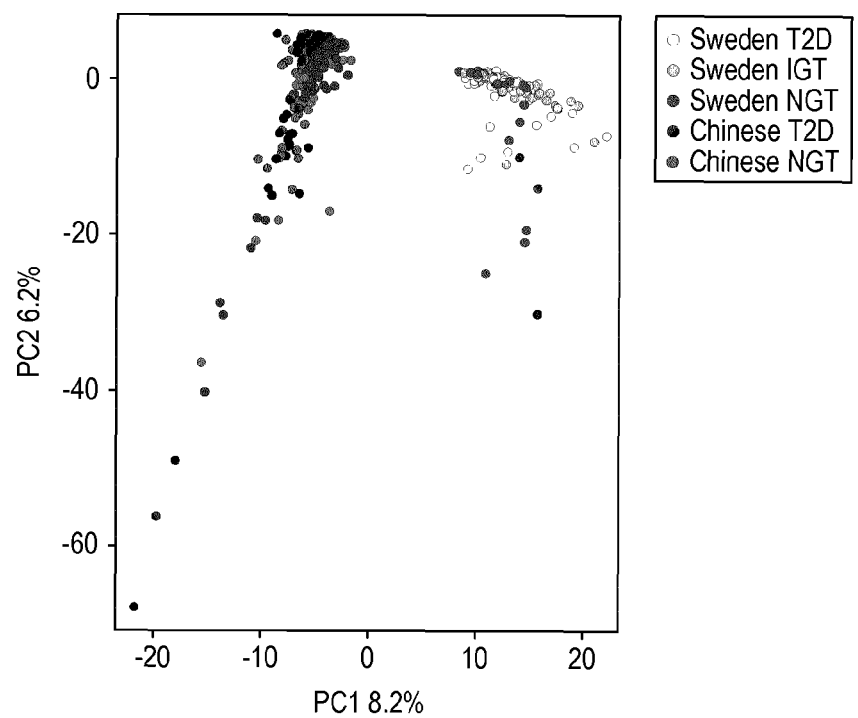
FIG. 8: Principal component analysis (PCA) of microbial species and MGCs abundance. a, Shared species with a maximum abundance above 1e-5 were included in the PCA analysis of the two cohorts showing a clear separation of Chinese and Swedish subjects. b, PCA analysis of MGCs also showing a clear separation between the two cohorts.
Figure 8B:
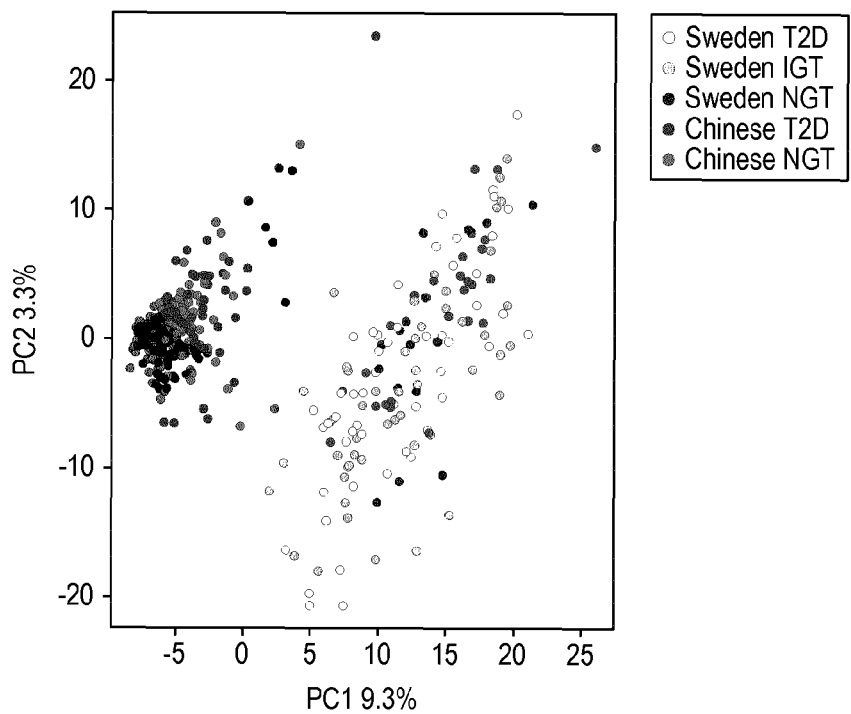
Figures 9A, 9B:
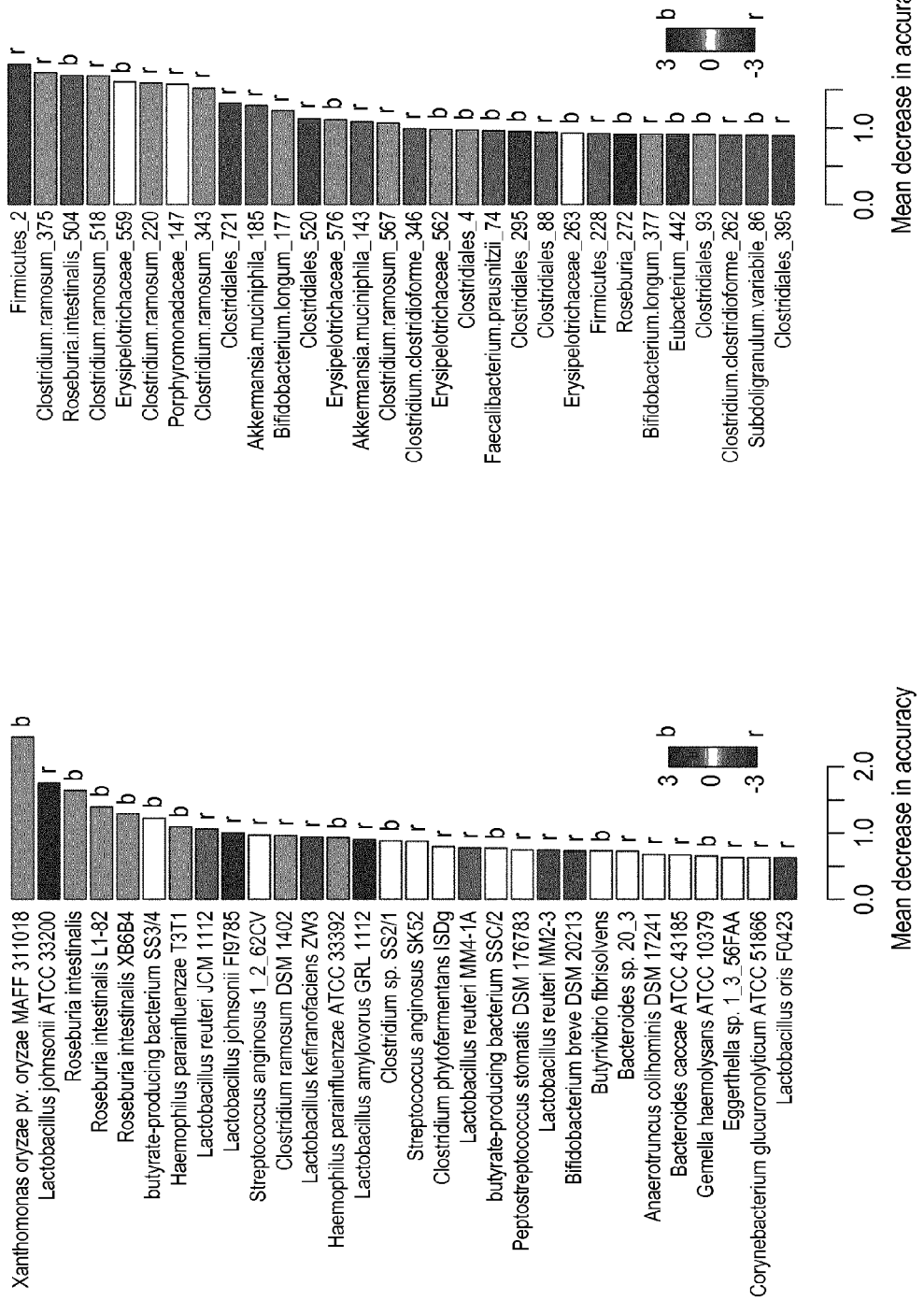
FIG. 9: Important species and MGCs in the predictive models for the classification of T2D and controls in the Chinese cohort. a, 30 most important species in the predictive model and discriminating NGT and T2D subjects. b, 30 most important MGCs in the predictive model and discriminating NGT and T2D subjects. Bar length indicates the importance of the variable and colours represent enrichment in T2D (red shades, marked 'r') or in NGT (blue shades, marked 'b').

To characterize the composition of the gut microbiota associated with T2D, we analyzed the fecal microbiota in 70-year-old women (n=145), as the prevalence of T2D and IGT is high among people older than 60 years. The cohort was selected with a stratified randomized method from a population-based screening sample (12, 13), resulting in three similarly sized subgroups: women who had T2D (n=53), IGT (n=49) or were healthy (normal glucose tolerance, NGT) (n=43) (see Tables 1 and 2 for subject characteristics). Genomic DNA was extracted with a standard procedure (14) and sequenced on Illumina HiSeq 2000. In total, we obtained 453 Gbp of paired end reads, with an average of 3.1±1.8 Gbp for each individual. To determine the composition of the gut microbiota, we aligned filtered Illumina reads to 2382 non-redundant reference genomes obtained from the NCBI and HMP databases (hmpdacc.org). The majority of the aligned reads (38±9.7% (SD)) belonged to the bacterial phyla *Firmicutes* and Bacteroidetes, each representing 67±12% (SD) and 19±12% (SD) of the microbiota (FIG. 4a). The archaeal phylum Euryarchaeota was also detected and showed high inter-subject variation (1.8±3.2% (SD); FIG. 4a). The most abundant genera, species and genomes in our cohort included members of *Ruminococcus, Bacteroides, Eubacterium* and *Faecalibacterium* (FIG. 4b and FIGS. 5a and b).

Figure 1B:
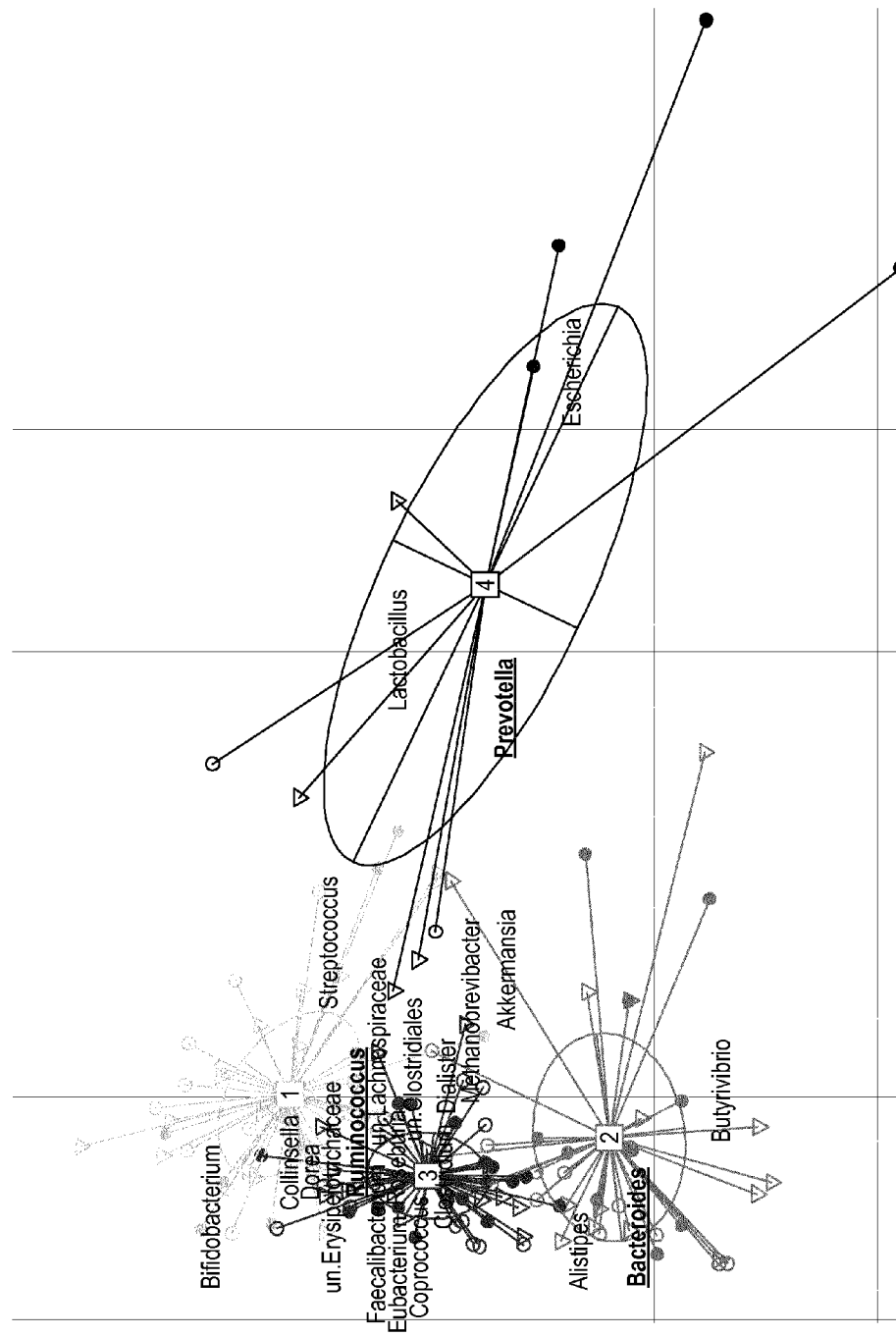
Figure 1C:
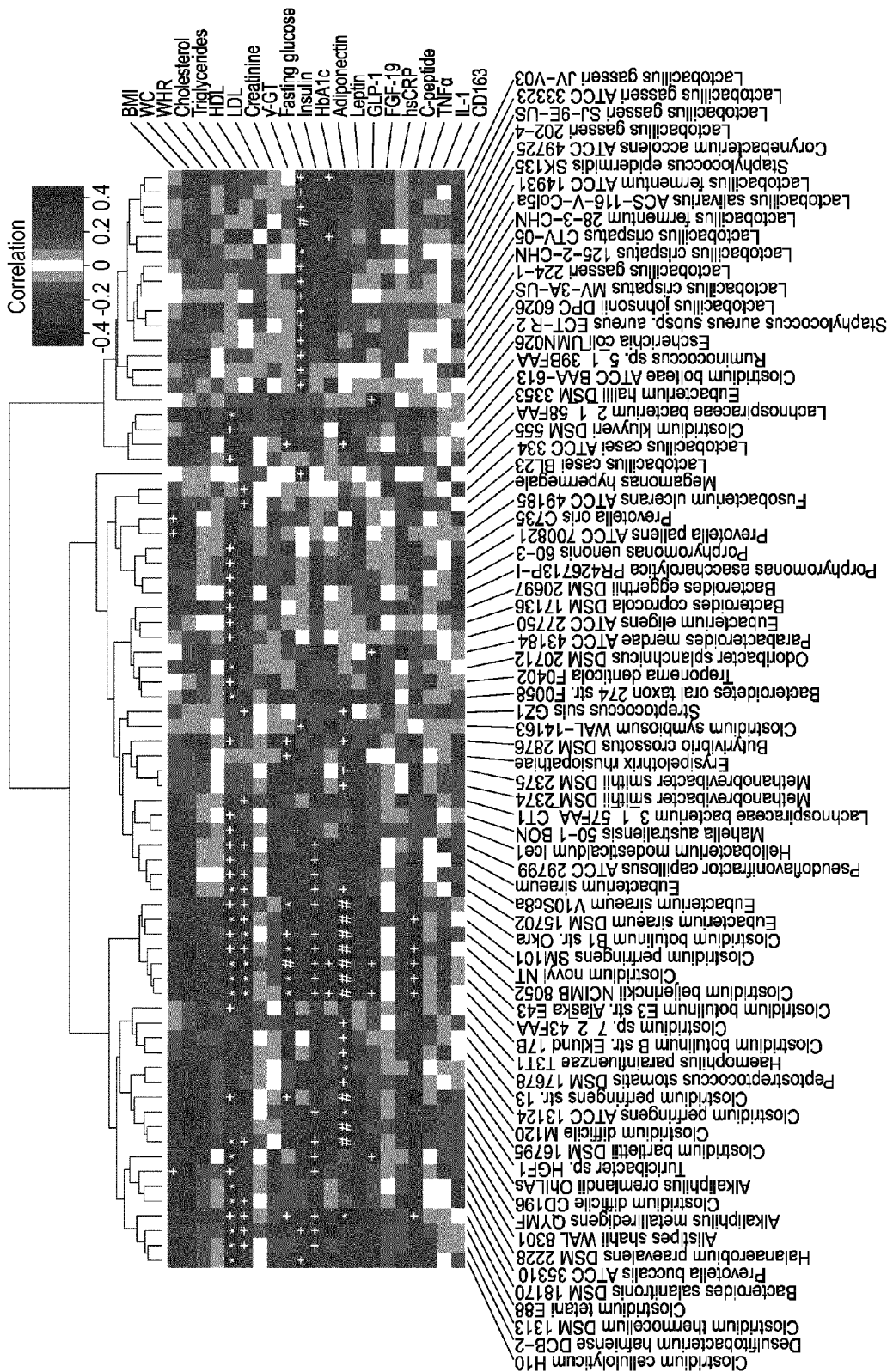

When comparing the composition T2D and NGT communities, the abundance of four *Lactobacillus* species increased, while that of five *Clostridium* species decreased in T2D women (Adj. P<0.05, Wilcoxon rank sum test) (FIG. 1a). *Lactobacillus* species correlated positively with fasting glucose and HbA1c, a long-term measure of blood glucose control (Adj. P<0.05) (FIG. 1c). *Clostridium* species, on the other hand correlated negatively with fasting glucose, HbA1c, insulin, C-peptide, plasma triglycerides, and positively with adiponectin and HDL cholesterol. These correlations are relevant for T2D because high triglycerides and low HDL-cholesterol levels are components of the dyslipidemia typically found in T2D, whereas serum levels of the insulin-sensitizing hormone adiponectin are reduced in people at risk of T2D (15).

Next we examined the structure of the gut microbiota in the subjects of our cohort and tested whether specific compositional clusters (enterotypes) were associated with T2D. We observed that the abundance of the 30 most abundant genera in the cohort was highly variable among the women in the cohort but no subject was dominated by a single genus (data not shown). We found evidence for the formation of four clusters (FIG. 1b) as a variant of the three originally described (16).

These clusters contained several abundant genera (data not shown) and, while *Prevotella* formed a distinct cluster, the relative abundance of both *Bacteroides* and *Ruminococcus* formed a gradient across all the subjects of our cohort (data not shown), indicating a lack of discrete clustering for these two microbiota configurations.

We continued the investigation of finding biomarkers that can be predictive for the risk of developing T2D, according to the present invention.

Example 3

Metagenomic Clusters to Study Gut Microbiota in T2D

To identify microbial species independently of reference genomes and fully exploit the information contained in the metagenomic data, we performed de novo assembly of filtered sequence data, first for each individual separately and then using all unassembled reads in one additional assembly to identify also rare genes. The total length of the assembly was 13.59 Gbp, from which 18.6 million genes could be predicted with a length longer than 100 bp. Genes were clustered based on 95% sequence similarity to create a non-redundant gene catalogue, resulting in 5 997 383 microbial genes in our cohort. These genes and the MetaHIT genes (17) were combined into a new gene catalogue, which was used to align reads. 4 778 619 genes were unique to our catalogue, and this number of unique genes in our catalogue could depend on the different methods used for genes clustering (BLAT and CD-HIT in the MetaHit and our study, respectively), although the same criteria of 95% sequence identity and 90% coverage on the shorter sequence were used. Alternatively, this discrepancy could depend on the different age of the MetaHit and our cohort (52±11y (SD) and 70±1y (SD), respectively; P<0.001), as it is known that the fecal microbiota of seniors older than 65 years is different from that of younger adults (18, 19).

Figure 2A:
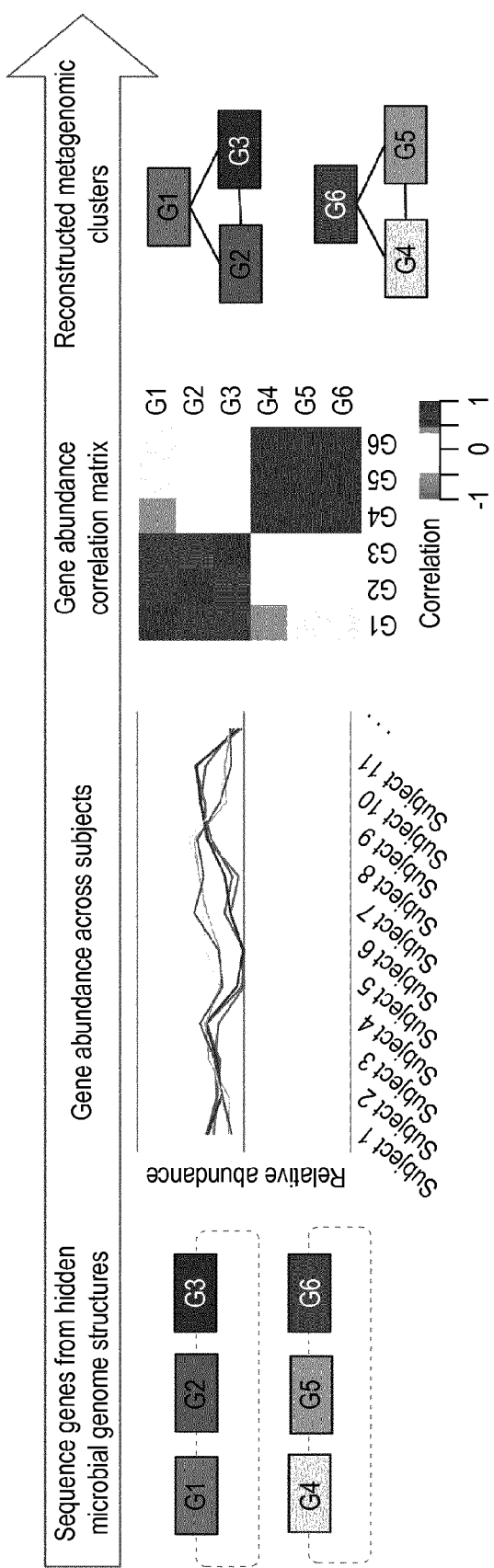
FIG. 2: Defining metagenomic clusters (MGCs) and associations with diabetes and clinical biomarkers. a, Schematic diagram showing how metagenomic clusters were defined. By using the assumption that genes in the same genome should have a similar abundance in a sample, genes that co-occur were clustered. b, Histogram of the number of genes in the 800 largest MGCs, all with more than 100 genes. c, Pie chart of the taxonomic annotation level of MGCs. d, MGCs differentially abundant are colored black in the abundance plot comparing the abundance in NGT and T2D subjects. Adj. P<0.05. e, Spearman's rank correlation of clinical data and MGCs abundance. + Adj. P<0.05; * Adj. P<0.01; # Adj. P<0.001.
Figure 2B:
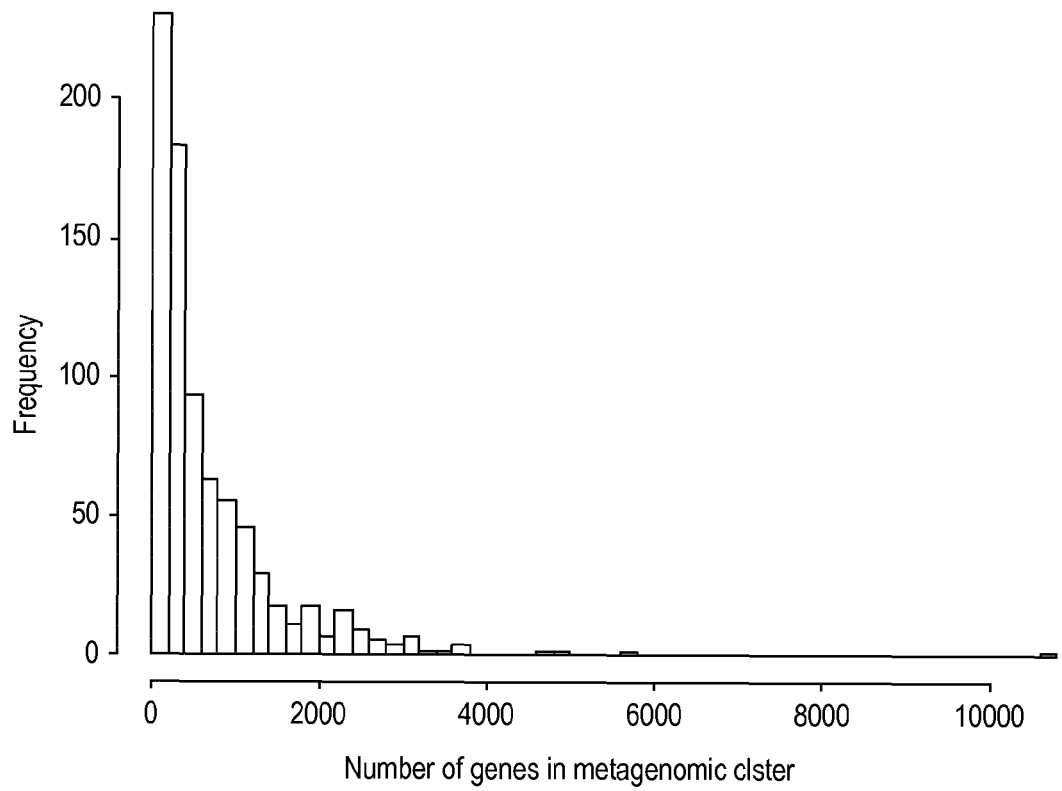

The fecal microbiota of NGT, IGT and T2D women contained similar number of genes, indicating that these communities harbored similar coding capacities. We assumed that genes belonging to one microbial species would co-occur in samples where that species is found. With this assumption, we analyzed the co-occurrence of genes present in at least 10 individuals (2.9 million genes) by calculating the correlation coefficient and then clustering sets of genes with high correlation among them (Pearson rho>0.85). We defined these sets of highly correlated genes as metagenomic clusters (MGCs) (FIG. 2a). The 800 largest MGCs contained at least 104 genes, and in total 550 084 genes were included (FIG. 2b). To determine the phylogenetic origin of the MGCs, we blasted the genes in each cluster against the NCBI nr catalogue and determined the lowest common ancestor (LCA) by requiring that at least 50% of the genes had a best hit to the same phylogenetic group.

Figure 2C:
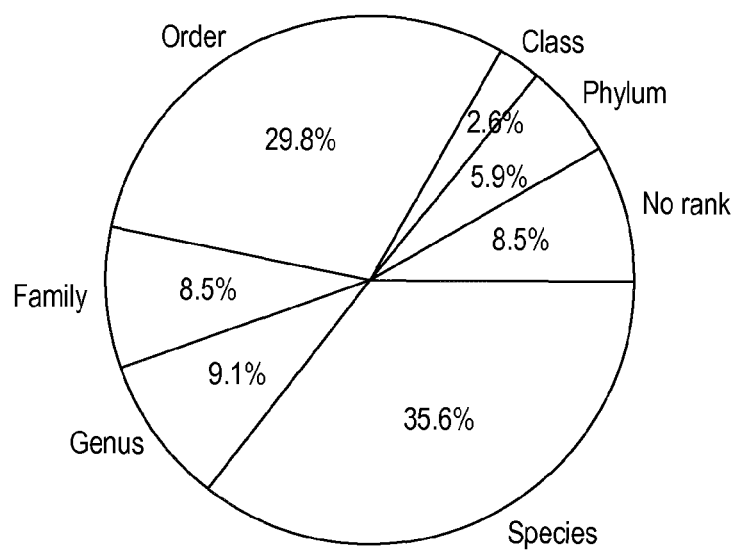

This analysis showed that only 35% of the clusters have an LCA at the species level (FIG. 2c), and that less well characterized clusters, with an LCA at the order level, were for the 98% *Clostridiales* and 2% Bacteroidales. The *Clostridiales* order is very diverse and reference genomes might be lacking in public databases, thus explaining the difficulty of the phylogenetic characterization.

Figure 2D:
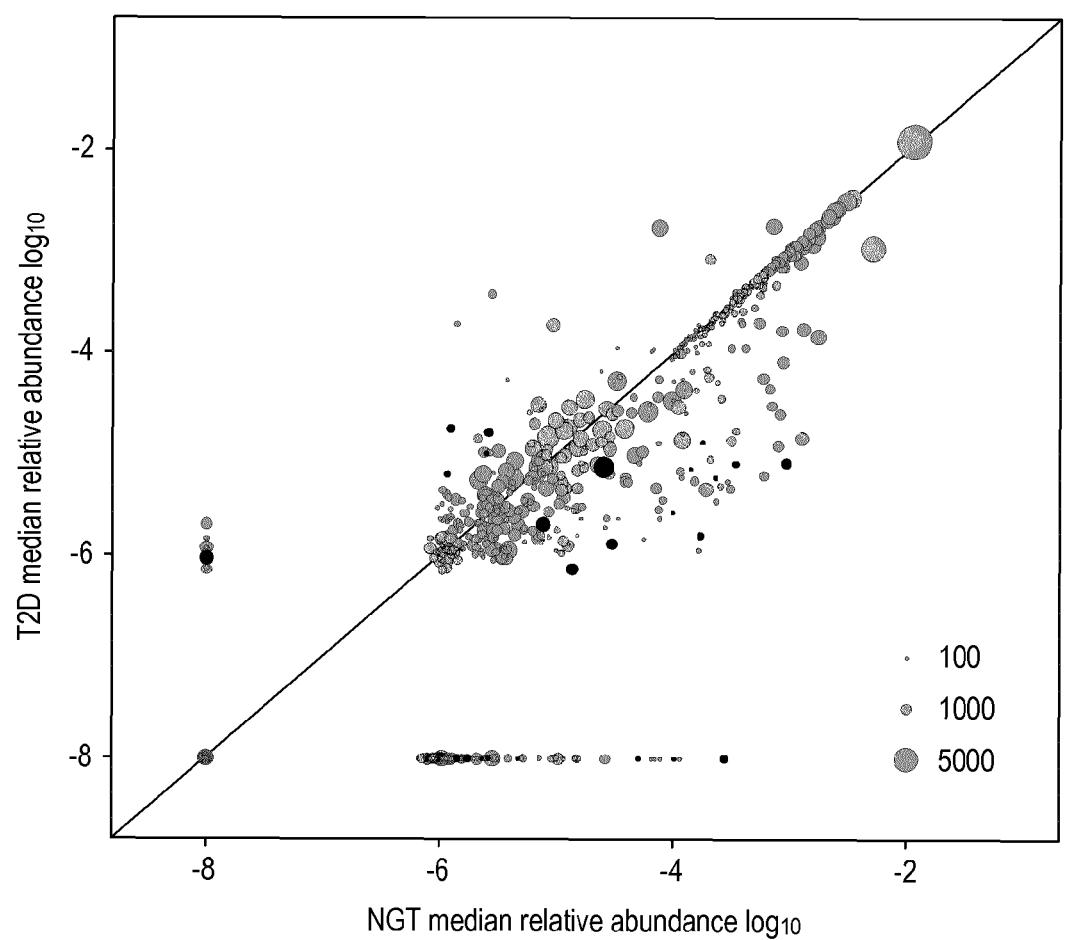
Figure 2E:
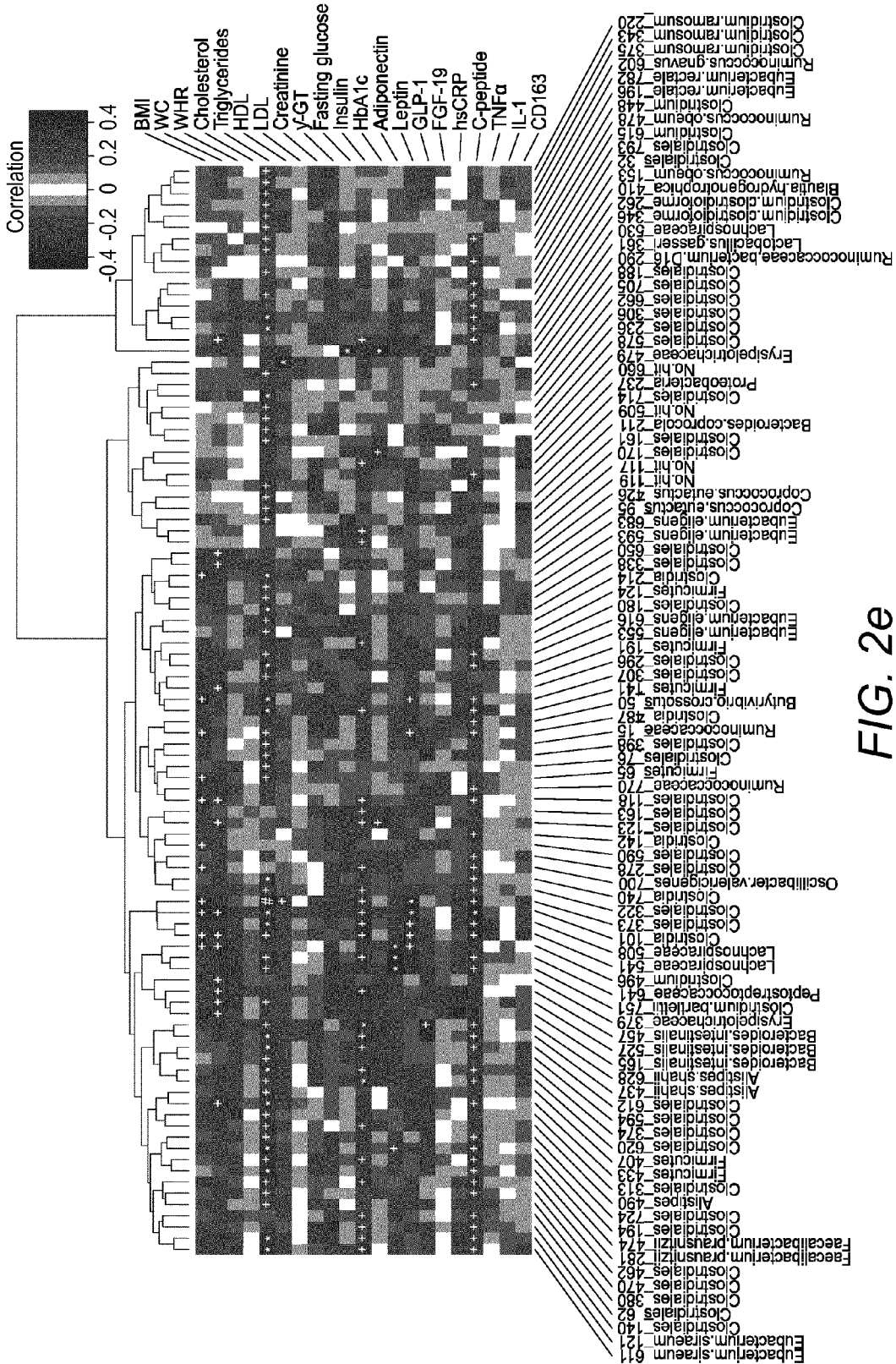

We tested the abundance of the 800 largest MGCs in NGT and T2D samples, and found 26 clusters to be differentially abundant between the two groups (Adj. P<0.05) (FIG. 2d). The MGCs most significantly enriched in T2D women were a *Clostridiales* identified at order level and two *Clostridium clostridioforme*. Other two MGCs were enriched in T2D microbiota, and were identified at species levels as *Lactobacillus gasseri* and *Streptococcus mutans*. *C. clostridioforme* correlated positively with triglyceride and C-peptide levels, while *L. gasseri* correlated positively with fasting glucose and HbA1c (FIG. 2e). 21 MGCs were significantly depleted in T2D, including *Roseburia* (i.e. *Roseburia*_272), two *Clostridium* genera, several *Clostridiales*, two *Eubacterium eligens*, Coriobacteriaceae and one *Bacteroides intestinalis*. In particular *Roseburia*_272 was greatly decreased in T2D communities. The clostridial MGCs correlated negatively with C-peptide, insulin and triglycerides levels, while *B. intestinalis* correlated negatively with insulin and waist circumference (WC) (FIG. 2e). These results largely agree with those obtained from the species-based analyses shown in FIG. 1.

Example 4

T2D Status can be Discriminated by the Microbiota

To test if the microbiota composition can identify T2D status we trained a Random Forest (RF) model in a test set of the NGT and T2D subjects. We evaluated its performance on unseen samples from the same groups and scored the predictive power in a receiver operator characteristic (ROC) analysis. The RF model generates a variable importance score for each species and MGC representing the predictive power. The importance score was used to rank species and MGCs, and the top most important ones were used in a model for predicting T2D. The discriminatory power of species and MGCs was calculated as the area under the ROC curve (AUC) (FIG. 3a). T2D was predicted more accurately with MGCs (highest AUC=0.83, 50 MGCs) than with microbial species (highest AUC=0.71, 238 species) (FIG. 3a, Table 3). When body mass index (BMI), waist-to-hip ratio (WHR) and waist circumference (WC) were used for predicting T2D we obtained a maximum AUC of 0.70 for WC (AUC for BMI=0.58; AUC for WHR=0.60), thus showing that the composition of the microbiota determined by MGCs correlates better with T2D than these known risk factors (22). Importantly, the T2D score obtained based on MGC clusters is similar to other published scores that combine several known risk factors for diabetes development (e.g. the FINDRISC score, validated in several countries (7)).

*L. gasseri* had the highest score for identification of T2D women using both models (FIG. 3b,c). *Roseburia*, several *Clostridiales*, *B. intestinalis*, *C. clostridioforme* and Coriobacteriaceae were amongst the 10 most important clusters in the model based on MGCs (FIG. 3b), while mostly lactobacilli and *clostridia* were amongst the 10 most important bacteria in the species model (FIG. 3c). The two models indicated different bacterial groups as most discriminant for T2D identification, but the bacteria identified by the MGC model had higher scores than those identified by the species model (FIG. 3b,c). Notably, the MGC model identified *Roseburia* and *Faecalibacterium prausnitzii* as highly discriminant for T2D. These bacteria are known human gut colonizers and butyrate producers (23), and have been linked to improved insulin sensitivity and diabetes amelioration in studies of the human fecal microbiota (9, 24).

Figure 3E:
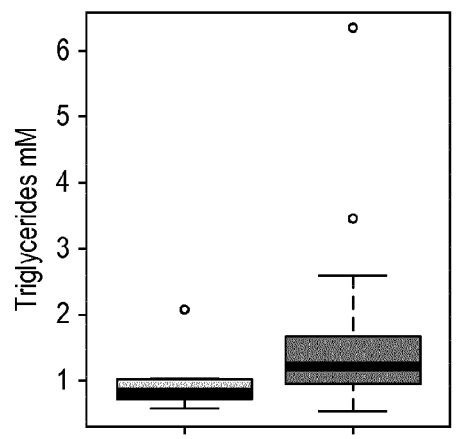
Figure 3F:
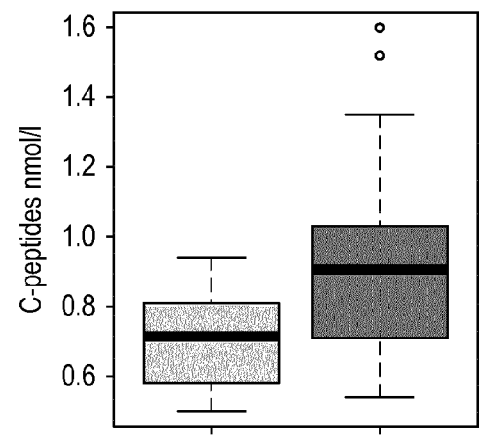

We used our RF model trained for the discrimination of NGT and T2D individuals to stratify the 49 IGT women of the cohort. Individuals were assigned to the NGT or T2D by applying the predictive model for NGT or T2D: 10 IGT women were included in the NGT subgroup while 34 were included in the T2D subgroup (5 could not be predicted, as the probability of being either NGT or T2D was 0.5±0.02), FIG. 3d. The characteristics of the two subgroups stratified according to faecal metagenomic profile showed that plasma levels of triglycerides and C-peptide were significantly higher in the subgroup identified as T2D than in the subgroup identified as NGT (P=0.019 and P=0.030, respectively, Wilcoxon rank sum test) (FIG. 3e,f).

Example 5

Functional Characterization of the T2D Metagenome

To characterize microbial functions we annotated all the genes of our catalogue to the KEGG database (version 59). We then used the reporter feature algorithm (25, 26) in combination with the KEGG metabolic network, pathway annotations and the information about relative gene abundance to identify reporter pathways (i.e. pathways with significantly differentially abundant KOs) that were associated with T2D and NGT status. We found that, despite having an equivalent number of genes (discussed above, data not shown), NGT and T2D communities had different functional composition and several reporter pathways were differentially abundant in T2D and NGT women. The pathways that showed the highest scores for enrichment in T2D metagenomes included KOs for starch and glucose/sucrose metabolism, fructose and mannose metabolism, and ABC transporters for amino acids, ions and simple sugars. In particular, 39 out of 46 KOs for starch and glucose/sucrose metabolism and 37 out of 49 KOs for fructose and mannose metabolism were more abundant in T2D compared to NGT metagenomes. For ABC transporters, 123 out of 174 KOs were more abundant in T2D metagenomes compared to NGT. These results are in agreement with previous studies showing an increase in microbial functions for energy metabolism and harvest in the obese microbiome (27, 28). Other metabolic pathways containing KOs enriched in women with T2D included glycerolipid metabolism and fatty acid biosynthesis. Finally, also enriched in T2D were the pathways for cysteine and methionine metabolism, which is related to glutathione synthesis and may be important for response to oxidative stress. Similarly, membrane transporters for sugars and branched-chain amino acids as well as genes related to oxidative stress resistance were also enriched in the metagenome of Chinese diabetic patients (11). Microbial functions enriched in NGT women were related to flagellar assembly and riboflavin metabolism. Interestingly, the metagenome of healthy individuals in the Chinese cohort was also enriched in functions related to flagellar assembly, and these functions belonged to bacteria in the *Roseburia*, *Butyrivibrio* and *Eubacterium* genera (11), while in our study they correlated to enterobacteria and *Roseburia*.

Example 6

Associations Between Gut Microbiota, Glucose Control and Medication

To identify other variables influencing the composition of the gut microbiota besides the diagnosis of T2D, we analyzed the effects of family history of diabetes, medication (i.e. statins and metformin) and degree of blood glucose control on T2D microbiota. We found no differentially abundant MGCs in T2D women with and without family history of diabetes; with or without medication; and with good or poor blood glucose control as measured by HbA1c levels (≥5.5%). However, we found bacterial species that were differentially abundant in women that did or did not use metformin (the most common oral antidiabetic drug) and in those with high or low HbA1c levels (data not shown). Women with T2D that used metformin had increased levels of several Enterobacteriaceae (i.e. *Escherichia*, *Shigella*, *Klebsiella* and *Salmonella*) and decreased levels of *Clostridium* and *Eubacterium*. The abundance of *E. coli* correlated significantly with the levels of glucagon-like peptide 1 (GLP-1) (FIG. 1c), and interestingly metformin has been shown to increase plasma GLP-1 levels (29). Previous studies also showed increased *E. coli* and Proteobacteria in the fecal microbiota of diabetic patients, but no information about medication was provided in these reports (11, 30). A different pattern appeared when comparing women with good or poor blood glucose control (HbA1c≥5.5%), characterized by an increase in Lactobacillales, mainly *Streptococcus* species, and a decrease in species belonging to *Bacteroides*, *Eubacterium* and *Clostridium* in women with high HbA1c. Thus, both the use of metformin and glucose control may impact on gut microbiota composition. However, these associations of microbial species with metformin and glucose control do not have a major confounding effect on the model for the discrimination T2D women based on fecal microbiota composition, as only two of the species included in the model were affected by the use of metformin (i.e. *Clostridium botulinum* B str. Eklund 17B and *Clostridium* sp. 7_2_43FAA) and two other were affected by poor glucose control (*Clostridium thermocellum* DSM 1313 and *Streptococcus* sp. C150). Importantly, these associations could only be identified with a species-based approach. Our MGC catalogue did not contain an *E. coli* cluster, which was the species that increased the most in women using metformin, and so we hypothesize that, due to the definition of MGC, low abundant genomes could be difficult to identify with this approach (*E. coli* was not among the 30 most abundant species and genomes, FIG. 5a,b).

At the functional level we identified reporter pathways that were significantly associated with the use of metformin and the degree of glucose control. The pathways with the highest scores in the metagenome of women with metformin included KOs for glutathione metabolism (e.g. glutathione synthase and reductase, gshB and gor genes), bacterial secretion (type I, II, III and VI) and *Vibrio cholera* pathogenic cycle. These results are in agreement with the increased levels of Enterobacteriaceae associated with the use of metformin and indeed the functions correlated to the genera *Escherichia*, *Shigella*, *Yersinia*, and *Salmonella*. However, a small number of functions enriched in women with metformin also correlated to *Streprococcus* and *Lactobacillus* abundance (K00383, glutathione reductase), and *Collinsella* (K04058, type III secretion system). In the women with poor glucose control we found significantly enriched KOs in pathways belonging to phosphotransferase system (PTS) transporters (functions for the transport of glucose and lactose, which correlated with *Collinsella* and *Streptococcus* abundance), glutathione metabolism, defense against host immune system (*Staphylococcus aureus* infections, K014205, resistance to antimicrobial peptides), and two-component systems. Two-component systems are sensory pathways that bacteria use to sense and respond to environmental changes. In women with poor glucose control we found enrichment in functions for response to phosphate and nitrogen limitation, nitrogen assimilation and metabolism, multidrug efflux, antibiotic resistance, and outer membrane stress. Most of these functions correlated to enterobacteria but a small portion correlated to *Eggerthella* (nitrogen assimilation and trimethylamine N-oxide metabolism), which contains opportunistic pathogens and was increased in Chinese T2D patients (11).

Example 7

Clinical Use of the Invention Herein

The method of the invention is used in a clinical setting to aid in the assessment if a person is in a risk group for developing T2D. First an assessment is made to determine if there is sufficient data available for specific biomarkers for T2D in the population group of the tested person. Sufficient in this context means a predictive power as an ROC AUC of 0.6 or above for selected MGC's for the population group, when people of that group with known disease status are tested.

Faecal samples and other samples are taken from the person and other normal assessments such as blood pressure, BMI, waist size are made. The faecal samples are processed as described above and metagenomic cluster score of the gastro intestinal flora is determined. The person is assigned to the NGT or T2D risk groups by applying the predictive model for NGT or T2D. This alone or in combination with customary clinically used risk values for the other variables, such as BMI and WC is used to determine if the person is at risk for developing T2D and should be further investigated, monitored or treated.

TABLE 1

Characteristics of 70-year old women with type 2 diabetes (T2D), impaired (IGT) and normal (NGT) glucose tolerance.

| | T2D (n = 53) | IGT (n = 49) | NGT (n = 43) | P-value |
|---|---|---|---|---|
| Body mass index, kg/m² | 28.4 ± 0.672 | 26.9 ± 0.576 | 25.8 ± 0.664 | 0.017 |
| Waist, cm | 94.2 ± 1.44 | 88.8 ± 1.18 | 84.1 ± 1.41 | 3.7e−06 |
| HbA1c, mmol/mol | 5.52 ± 0.1240 | 4.60 ± 0.0508 | 4.53 ± 0.0353 | 2.6e−16 |
| Serum insulin, | $12.70^a$ ± 1.940 | $8.94^a$ ± 0.773 | $6.97^a$ ± 0.529 | 5.6e−06 |
| Serum C-peptide, | $0.958^a$ ± 0.0779 | $0.838^a$ ± 0.0405 | $0.671^a$ ± 0.0355 | 0.00025 |
| Serum HDL cholesterol, mmol/l | 1.62 ± 0.0664 | 1.79 ± 0.0769 | 1.96 ± 0.0763 | 0.0058 |
| Serum triglycerides, mmol/l | $1.260^a$ ± 0.1140 | $1.190^a$ ± 0.1350 | $0.961^a$ ± 0.0755 | 0.017 |
| Serum triglycerides >1.7 mmol/L, n (%) | 14(26) | 11(22) | 1(2) | 0.0055 |
| Statin treatment, n (%) | 26(49) | 16(33) | 10(23) | 0.027 |
| Insulin treatment, n (%) | 6(11) | 0(0) | 0(0) | 0.0044 |
| Oral antidiabetic medication, n (%) | 22(41) | 0(0) | 0(0) | 1.7e−10 |

Differences between groups were analysed with linear regression for continuous variables after log transformation of skewed variables and Chi-squared test for categorical variables. Values are mean±standard error of the mean if not stated otherwise. $^a$Geometric mean.

TABLE 2

Change in glucose tolerance status during a mean of 5.6 years follow-up.

| Classification at present re-examination | Classification at baseline | | |
|---|---|---|---|
| | T2D | IGT | NGT |
| T2D, n | 47 | 6 | 0 |
| IGT, n | 0 | 31 | 18 |
| NGT, n | 0 | 6 | 37 |

TABLE 3

AUC for the RF models based on MGCs and species.

| Number of metagenomic clusters | AUC MGCs | Number of species | AUC species |
|---|---|---|---|
| 800 | 0.80474 | 952 | 0.70821 |
| 400 | 0.80781 | 476 | 0.71523 |
| 200 | 0.81220 | 238 | 0.71457 |
| 100 | 0.82492 | 119 | 0.71435 |
| 50 | 0.83414 | 60 | 0.69241 |
| 25 | 0.76920 | 30 | 0.69351 |
| 12 | 0.70864 | 15 | 0.70864 |
| 6 | 0.67201 | 7 | 0.68078 |
| 3 | 0.66937 | 4 | 0.64151 |
| 1 | 0.58271 | 1 | 0.60509 |

The present invention is not limited to the above-described preferred embodiments. Various alternatives, modifications and equivalents may be used. Therefore, the above embodiments should not be taken as limiting the scope of the invention, which is defined by the appending claims.

REFERENCES

1. S. Wild, G. Roglic, A. Green, R. Sicree, H. King, Global prevalence of diabetes: estimates for the year 2000 and projections for 2030. *Diabetes care* 27, 1047 (May, 2004).
2. G. Danaei et al., National, regional, and global trends in fasting plasma glucose and diabetes prevalence since 1980: systematic analysis of health examination surveys and epidemiological studies with 370 country-years and 2.7 million participants. *Lancet* 378, 31 (Jul. 2, 2011).
3. V. Lundberg, B. Stegmayr, K. Asplund, M. Eliasson, F. Huhtasaari, Diabetes as a risk factor for myocardial infarction: population and gender perspectives. *Journal of internal medicine* 241, 485 (June, 1997).
4. F. Vendrame, P. A. Gottlieb, Prediabetes: prediction and prevention trials. *Endocrinology and metabolism clinics of North America* 33, 75 (March, 2004).

5. W. C. Knowler et al., Reduction in the incidence of type 2 diabetes with lifestyle intervention or metformin. *The New England journal of medicine* 346, 393 (Feb. 7, 2002).
6. J. Tuomilehto et al., Prevention of type 2 diabetes mellitus by changes in lifestyle among subjects with impaired glucose tolerance. *The New England journal of medicine* 344, 1343 (May 3, 2001).
7. D. Noble, R. Mathur, T. Dent, C. Meads, T. Greenhalgh, Risk models and scores for type 2 diabetes: systematic review. *BMJ (Clinical research ed* 343, d7163 (2011).
8. F. Backhed et al., The gut microbiota as an environmental factor that regulates fat storage. *Proceedings of the National Academy of Sciences of the United States of America* 101, 15718 (Nov. 2, 2004).
9. A. Vrieze et al., Transfer of Intestinal Microbiota from Lean Donors Increases Insulin Sensitivity in Subjects with Metabolic Syndrome. *Gastroenterology*, (Jun. 20, 2012).
10. R. E. Ley, P. J. Turnbaugh, S. Klein, J. I. Gordon, Microbial ecology: human gut microbes associated with obesity. *Nature* 444, 1022 (Dec. 21, 2006).
11. J. Qin et al., A metagenome-wide association study of gut microbiota in type 2 diabetes. *Nature*, (Sep. 26, 2012).
12. G. Brohall, C. J. Behre, J. Hulthe, J. Wikstrand, B. Fagerberg, Prevalence of diabetes and impaired glucose tolerance in 64-year-old Swedish women: experiences of using repeated oral glucose tolerance tests. *Diabetes Care* 29, 363 (February 2006).
13. B. Fagerberg, D. Kellis, G. Bergstrom, C. J. Behre, Adiponectin in relation to insulin sensitivity and insulin secretion in the development of type 2 diabetes: a prospective study in 64-year-old women. *J Intern Med* 269, 636 (June, 2011).
14. A. Salonen et al., Comparative analysis of fecal DNA extraction methods with phylogenetic microarray: effective recovery of bacterial and archaeal DNA using mechanical cell lysis. *J Microbiol Methods* 81, 127 (May, 2010).
15. S. Li, H. J. Shin, E. L. Ding, R. M. van Dam, Adiponectin levels and risk of type 2 diabetes: a systematic review and meta-analysis. *JAMA: the journal of the American Medical Association* 302, 179 (Jul. 8, 2009).
16. M. Arumugam et al., Enterotypes of the human gut microbiome. *Nature* 473, 174 (May 12, 2011).
17. J. Qin et al., A human gut microbial gene catalogue established by metagenomic sequencing. *Nature* 464, 59 (2010).
18. E. Biagi et al., Through Ageing, and Beyond: Gut Microbiota and Inflammatory Status in Seniors and Centenarians. *PLoS ONE* 5, e10667 (2010).
19. M. J. Claesson et al., Composition, variability, and temporal stability of the intestinal microbiota of the elderly. *Proc Natl Acad Sci USA* 108 Suppl 1, 4586 (Mar. 15, 2011).
20. S. M. Finegold et al., *Clostridium clostridioforme*: a mixture of three clinically important species. *European journal of clinical microbiology & infectious diseases: official publication of the European Society of Clinical Microbiology* 24, 319 (May, 2005).
21. D. Knights, E. K. Costello, R. Knight, Supervised classification of human microbiota. *FEMS Microbiol Rev* 35, 343 (March, 2011).
22. Y. Wang, E. B. Rimm, M. J. Stampfer, W. C. Willett, F. B. Hu, Comparison of abdominal adiposity and overall obesity in predicting risk of type 2 diabetes among men. *The American journal of clinical nutrition* 81, 555 (March, 2005).
23. P. Louis, P. Young, G. Holtrop, H. J. Flint, Diversity of human colonic butyrate-producing bacteria revealed by analysis of the butyryl-CoA:acetate CoA-transferase gene. *Environ Microbiol* 12, 304 (February, 2010).
24. J. P. Furet et al., Differential adaptation of human gut microbiota to bariatric surgery-induced weight loss: links with metabolic and low-grade inflammation markers. *Diabetes* 59, 3049 (December, 2010).
25. A. P. Oliveira, K. R. Patil, J. Nielsen, Architecture of transcriptional regulatory circuits is knitted over the topology of bio-molecular interaction networks. *BMC Syst Biol* 2, 17 (2008).
26. K. R. Patil, J. Nielsen, Uncovering transcriptional regulation of metabolism by using metabolic network topology. *Proc Natl Acad Sci USA* 102, 2685 (Feb. 22, 2005).
27. P. J. Turnbaugh et al., An obesity-associated gut microbiome with increased capacity for energy harvest. *Nature* 444, 1027 (Dec. 21, 2006).
28. P. J. Turnbaugh et al., A core gut microbiome in obese and lean twins. *Nature* 457, 480 (2009).
29. A. Maida, B. J. Lamont, X. Cao, D. J. Drucker, Metformin regulates the incretin receptor axis via a pathway dependent on peroxisome proliferator-activated receptor-alpha in mice. *Diabetologia* 54, 339 (February, 2011).
30. N. Larsen et al., Gut microbiota in human adults with type 2 diabetes differs from non-diabetic adults. *PloS one* 5, e9085 (2010).

The invention claimed is:

1. A computer program product on a non-transitory computer readable medium that when executed operates to identify an individual having or at risk of developing type 2 diabetes (T2D) using metagenomic clusters (MGCs), wherein said computer program product is configured to provide different metagenomic clusters relevant to type 2 diabetes for different population groups.

2. The computer program product of claim 1, wherein said population groups are selected from one or more of age, geographical location, race/ethnic group, environmental factors such as food habits, and gender, or combinations thereof.

3. The computer program product of claim 1, wherein at least one of said population groups is based on age, or geographical location, or age combined with geographical location, or age combined with race, or age combined with geographical location and race.

4. The computer program product of claim 3, wherein said population group is aged 65 and over, more preferably European or Caucasian of age 65 and over, most preferably European Caucasian of age 65 and over.

5. The computer program product of claim 1, wherein said population group is based on gender.

6. The computer program product of claim 1, wherein construction of the computer program product is further configured to:
  (i) select the population group to be studied;
  (ii) obtain gut metagenomic sequence data from said population; and
  (iii) identify MGCs from all the metagenomic sequence data from said population.

7. The computer program product of claim 6, further wherein:
  (a) a random forest or similar model is used to train on a test set of normal and T2D samples to generate a predictive model for T2D;
  wherein the computer program product is further configure to (b) use a list of importance scores of the MGCs in the model; and
(c) use a top scoring MGCs in the model for predicting T2D.

8. The computer program product of claim 1, wherein the MGCs for each of said population groups are provided by:
  (i) performing a de novo assembly of filtered sequence data from the gut metagenome, first for each individual of the population separately and then using all unassembled reads in one additional assembly to identify also rare genes;
  (ii) clustering genes based on sequence similarity to create a non-redundant gene catalogue resulting in a number of microbial genes in the population;
  (iii) analysing the co-occurrence of genes present in at least 2 individuals by calculating the correlation coefficient and then clustering sets of genes with high correlation among them to provide MGCs.

9. The computer program product of claim 8, wherein the sequence similarity in step (ii) is 95% and/or the high correlation in step (iii) is a Pearson rho value of >0.85.

10. The computer program product of claim 1, wherein the computer program product is further configured to use other measurements or risk factors relevant to the identification of T2D.

11. The computer program product of claim 10, wherein said other measurements are body mass index (BMI), waist-to-hip ratio (WHR) and/or waist circumference (WC).

12. A method of generating metagenomic data for use in identifying an individual having or at risk of developing type 2 diabetes (T2D), comprising:
  (i) selecting a population group to be studied, wherein said population group is based on age or gender, optionally in combination with one or more of geographical location, race/ethnic group, and environmental factors such as food habits;
  (ii) obtaining gut metagenomic sequence data from said population; and
  (iii) identifying MGCs from all the metagenomic sequence data from said population.

13. The method of claim 12, wherein said population group is based on age, or geographical location, or age combined with geographical location, or age combined with race, or age combined with geographical location and race.

14. The method of claim 12 further comprising the features of claim 7.

15. A method for identifying an individual having or at risk of developing T2D, comprising obtaining a gut microbial sample from said individual and using the computer program product of claim 1 to determine whether the individual has or is at risk of developing T2D.

16. The method of claim 15, further comprising assigning an individual to a normal group or to a T2D group using a computer program product on a non-transitory computer readable medium that when executed operates to identify an individual having or at risk of developing type 2 diabetes (T2D) using metagenomic clusters (MGCs), wherein said computer program product is configured to provide different metagenomic clusters for different population groups and assignation to the T2D group indicates that the individual has or is at risk of developing T2D.

17. A method for identifying an individual having or at risk of developing T2D comprising obtaining a gut microbial sample from said individual and determining the levels or abundance of at least 5, 6, 8, 10, 12, 15, or all, of the species and orders selected from the group consisting of *Lactobacillus. gasseri; Roseburia; Clostridiales; Bacteroides.intestinalis; Clostridium lostridioforme*; Coriobacteriaceae; *Clostridium; Firmicutes; Bacteroides.coproccola; Faecalibacterium.prausnitzil; Clostridia; Bacteroides.dorei; Eubacteriuraeligens; Streptococcus.mutans*; Lachnospiraceae; and *Alistipes*.

18. The method of claim 17, wherein the species and orders analysed are at least *Lactobacillus. gasseri; Roseburia; Clostridiales; Bacteroides.intestinalis*; and *Clostridium*, clostridio forme.

19. A computer system, comprising: a processor; and a memory coupled to the processor, the memory comprising computer readable program code embodied therein that, when executed by the processor, causes the processor to perform operations according to claim 1.

20. The system of claim 19, wherein one of said population groups is based on age or gender, optionally in combination with one or more of geographical location, race/ethnic group, and environmental factors such as food habits.

* * * * *